United States Patent
da Costa e Silva et al.

(10) Patent No.: US 7,847,155 B2
(45) Date of Patent: Dec. 7, 2010

(54) PHOSPHATASE STRESS-RELATED PROTEINS AND METHODS OF USE IN PLANTS

(75) Inventors: Oswaldo da Costa e Silva, Neustadt (DE); Nocha Van Thielen, Durham, NC (US); Ruoying Chen, Duluth, GA (US); Hans Bohnert, Tucson, AZ (US); Manabu Ishitani, Medley, FL (US)

(73) Assignee: BASF Plant Science GmbH (DE)

( * ) Notice: Subject to any disclaimer, the term of this patent is extended or adjusted under 35 U.S.C. 154(b) by 79 days.

(21) Appl. No.: 12/370,659

(22) Filed: Feb. 13, 2009

(65) Prior Publication Data

US 2009/0165170 A1     Jun. 25, 2009

Related U.S. Application Data

(60) Continuation of application No. 12/316,479, filed on Dec. 12, 2008, now Pat. No. 7,803,987, and a continuation of application No. 11/833,367, filed on Aug. 3, 2007, now Pat. No. 7,482,510, and a continuation of application No. 10/764,259, filed on Jan. 23, 2004, now Pat. No. 7,271,316, and a division of application No. 09/828,302, filed on Apr. 6, 2001, now Pat. No. 6,818,805.

(60) Provisional application No. 60/196,001, filed on Apr. 7, 2000.

(51) Int. Cl.
*C12N 15/82* (2006.01)
*C12N 15/29* (2006.01)
*A01H 5/00* (2006.01)
*A01H 5/10* (2006.01)

(52) U.S. Cl. ............... 800/289; 435/320.1; 435/419; 800/298

(58) Field of Classification Search ............... None
See application file for complete search history.

(56) References Cited

U.S. PATENT DOCUMENTS 6,548,743 B1 * 4/2003 Sheen et al. ........ 800/288

* cited by examiner

*Primary Examiner*—Cynthia Collins
(74) *Attorney, Agent, or Firm*—Patricia A. McDaniels

(57) ABSTRACT

A transgenic plant transformed by a phosphatase stress-related protein (PHSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated PHSRPs, and isolated nucleic acid coding PHSRPs, and vectors and host cells containing the latter.

17 Claims, 10 Drawing Sheets

PpPP2A-2 | WT

PpPP2C-1 | WT

PpPP2C-2

WT

PHOSPHATASE STRESS-RELATED PROTEINS AND METHODS OF USE IN PLANTS

CROSS REFERENCE TO RELATED APPLICATIONS

This application is a divisional of U.S. patent application Ser. No. 09/828,302, filed Apr. 6, 2001 and now U.S. Pat. No. 6,818,805; and is with U.S. patent application Ser. No. 12/316,479, filed Dec. 12, 2008, which is also a divisional of U.S. patent application Ser. No. 09/828,302 and is with U.S. patent application Ser. No. 11/833,367, filed Aug. 3, 2007 and now U.S. Pat. No. 7,482,510, which is a continuation of U.S. patent application Ser. No. 10/764,259, filed Jan. 23, 2004, and now U.S. Pat. No. 7,271,316, which is also a divisional of U.S. nonprovisional patent application Ser. No. 09/828,302, which claims the priority benefit of U.S. provisional Application Ser. No. 60/196,001 filed Apr. 7, 2000. Each of the above-identified applications is hereby incorporated herein in its entirety.

BACKGROUND OF THE INVENTION

1. Field of the Invention

This invention relates generally to nucleic acid sequences encoding proteins that are associated with abiotic stress responses and abiotic stress tolerance in plants. In particular, this invention relates to nucleic acid sequences encoding proteins that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as rice, maize (corn) and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on plant development, growth and yield of most crop plants are profound. Furthermore, most of the crop plants are very susceptible to higher salt concentrations in the soil. Continuous exposure to drought and high salt causes major alterations in the plant metabolism. These great changes in metabolism ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold and salt tolerance in model, drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerant plants using biotechnological methods.

It is well recognized that reversible phosphorylation of proteins controls many cellular processes in plants and animals. The phosphorylation status of proteins is regulated by the opposing activities of protein kinases and protein phosphatases. Phosphorylation of eukaryotic proteins occurs predominantly on serine and threonine residues, and to a lesser extent, on tyrosine residues. In animals, protein phosphorylation plays well-known roles in diverse cellular processes such as glycogen metabolism, cell cycle control, and signal transduction (Smith, R. D. and Walker, J. C., 1996, Annu. Rev. Plant Physiol. Plant Mol. Biol. 47:101-125).

Protein phosphatase activities have been reported in most plant subcellular compartments, including mitochondria, chloroplast, nuclei and the cytosol, and are associated with various membrane and particulate fractions. Some protein phosphatases are poorly characterized and may represent novel enzymes that are unique to plants. Others have biochemical properties that are very similar to well-known mammalian protein phosphatases, such as cytosolic protein serine/threonine phosphatases (MacKintosh C. and Cohen P. 1989 Biochem. J. 262:335-339). Two such plant serine/threonine phosphatases have been identified that function similar to mammalian type-1 (PP1) and type-2 (PP2) protein serine/threonine phosphatases. Biochemical and genetic studies in plants implicate PP1 and/or PP2 activity in signal transduction, hormonal regulation, mitosis, and control of carbon and nitrogen metabolism (Smith, R. D. and Walker, J. C., 1996, Annu. Rev. Plant Physiol. Plant Mol. Biol. 47:101-125).

Experimental evidence has implicated the involvement of protein phosphatases in the plant stress signaling cascade, and more particularly, in stress perception and signal transduction linked to physiological mechanisms of adaptation in plants. For example, protein phosphatase 2C (PP2C) has been shown to be involved in stress responses in plants (Sheen, J 1998 Proc. Natl. Acad. Sci. USA 95:975-980). It has also been demonstrated that, in yeast, the PP2B phosphatase calcineurin (CaN) is a focal component of a $Ca^{2+}$-dependent signal transduction pathway that mediates $Na^+$, $Li^-$, and $Mn^{2+}$ tolerance of *Saccharomyces cerecisiae* (Cunningham, K. W. and Fink, G. R. 1996 Mol. Cell. Biol. 16:2226-2237). CaN functions to limit intracellular $Na^+$ accumulation by regulating processes that restrict influx and enhance efflux of this cation across the plasma membrane. CaN also participates in cytosolic $Ca^{2+}$ homeostasis through the positive regulation of Golgi apparatus and vacuolar membrane-localized P-type ion pumps and negative control of a vacuolar $H^+/Ca^{2+}$ exchanger. Interestingly, overexpression of yeast CaN confers salt tolerance in plants, strongly indicating that modulation of stress signaling pathways by expression of an activated protein phosphatase substantially enhances plant stress tolerance (Pardo, J. M. et al. 1998 Proc. Natl. Acad. Sci. USA 95:9681-9686).

Although some genes that are involved in stress responses in plants have been characterized, the characterization and cloning of plant genes that confer stress tolerance remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in tolerance, direct evidence is still lacking, and the functions of many stress-responsive genes are unknown.

There is a need, therefore, to identify genes expressed in stress tolerant plants that have the capacity to confer stress resistance to its host plant and to other plant species. Newly generated stress tolerant plants will have many advantages, such as increasing the range that crop plants can be cultivated by, for example, decreasing the water requirements of a plant species.

SUMMARY OF THE INVENTION

This invention fulfills in part the need to identify new, unique phosphatases capable of conferring stress tolerance to plants upon over-expression. The present invention provides a transgenic plant cell transformed by a PHosphatase Stress-Related Protein (PHSRP) coding nucleic acid, wherein expression of the nucleic acid sequence in the plant cell results in increased tolerance to environmental stress as compared to a wild type variety of the plant cell, Namely, described herein are the protein phosphatases 1) Protein Phosphatase 2A-2 (PP2A-2), Protein Phosphatase 2A-3 (PP2A-3), Protein Phosphatase 2A-4 (PP2A-4); Protein Phosphatase 2C-1 (PP2C-1) and Protein Phosphatase 2C-2 (PP2C-2), all from *Physcomitrella patens*.

The invention provides in some embodiments that the PHSRP and coding nucleic acid are those found in members of the genus *Physcomitrella*. In another preferred embodiment, the nucleic acid and protein are from *Physcomitrella patens*. The invention provides that the environmental stress can be salinity, drought, temperature, metal, chemical, pathogenic and oxidative stresses, or combinations thereof. In preferred embodiments, the environmental stress can be drought or cold temperature.

The invention further provides a seed produced by a transgenic plant transformed by a PHSRP coding nucleic acid, wherein the plant is true breeding for increased tolerance to environmental stress as compared to a wild type variety of the plant. The invention further provides a seed produced by a transgenic plant expressing a PHSRP, wherein the plant is true breeding for increased tolerance to environmental stress as compared to a wild type variety of the plant.

The invention further provides an agricultural product produced by any of the below-described transgenic plants, plant parts or seeds. The invention further provides an isolated PHSRP as described below. The invention further provides an isolated PHSRP coding nucleic acid, wherein the PHSRP coding nucleic acid codes for a PHSRP as described below.

The invention further provides an isolated recombinant expression vector comprising a PHSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a PHSRP coding nucleic acid, wherein expression of the nucleic acid in the plant results in increased tolerance to environmental stress as compared to a wild type variety of the plant comprising: (a) transforming a plant cell with an expression vector comprising a PHSRP coding nucleic acid, and (b) generating from the plant cell a transgenic plant with an increased tolerance to environmental stress as compared to a wild type variety of the plant. In preferred embodiments, the PHSRP and PHSRP coding nucleic acid are as described below.

The present invention further provides a method of identifying a novel PHSRP, comprising (a) raising a specific antibody response to a PHSRP, or fragment thereof, as described above; (b) screening putative PHSRP material with the antibody, wherein specific binding of the antibody to the material indicates the presence of a potentially novel PHSRP; and (c) identifying from the bound material a novel PHSRP in comparison to known PHSRP. Alternatively, hybridization with nucleic acid probes as described below can be used to identify novel PUSH) nucleic acids.

The present invention also provides methods of modifying stress tolerance of a plant comprising, modifying the expression of a PHSRP in the plant, wherein the PHSRP is as described below. The invention provides that this method can be performed such that the stress tolerance is either increased or decreased. Preferably, stress tolerance is increased in a plant via increasing expression of a PHSRP.

DETAILED DESCRIPTION OF THE INVENTION

Figure 1:
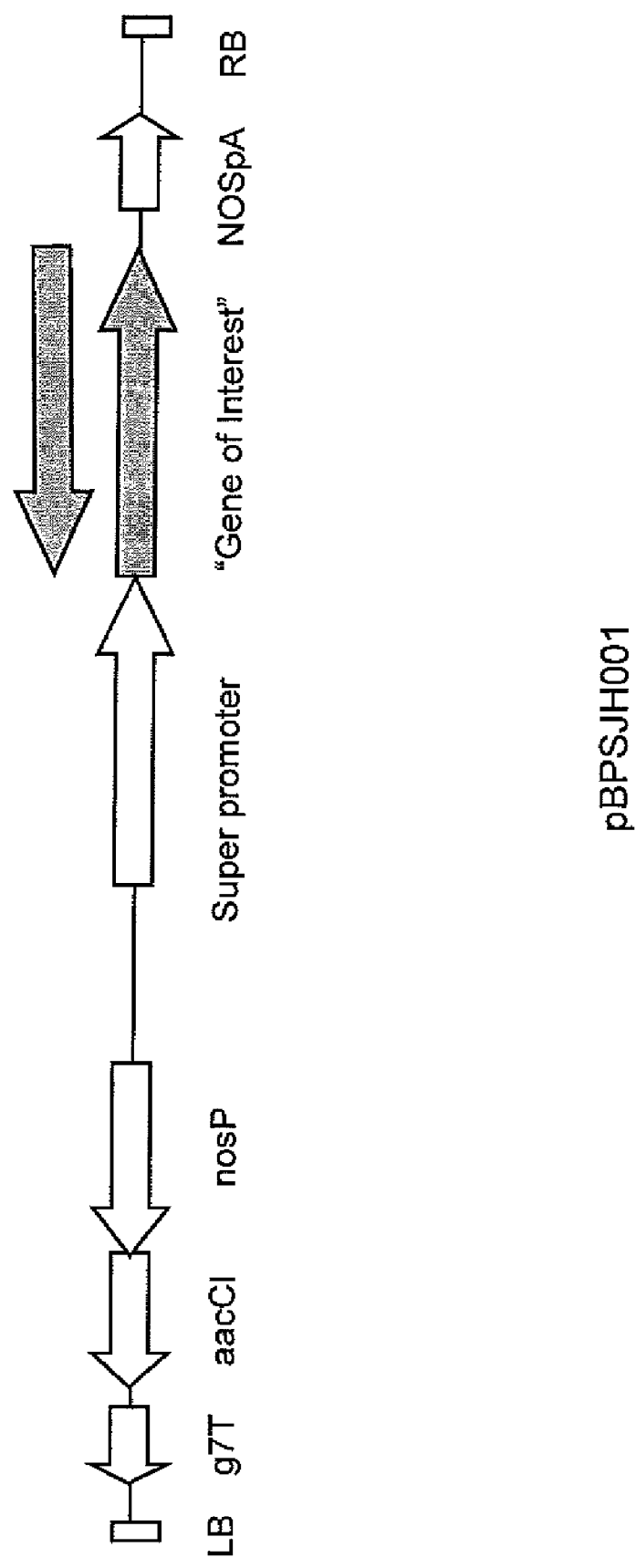
FIG. 1 shows a diagram of the plant expression vector pBPSsc022 containing the super promoter driving the expression of SEQ ID NOs: 6, 7, 8, 9 and 10 ("Desired Gene"). The components are: NPTII kanamycin resistance gene (Bevan M, Nucleic Acids Res. 26: 8711-21, 1984), AtAct2-i promoter (An Y Q et al., Plant J 10: 107-121 1996), OCS3 terminator (During K, Transgenic Res. 3: 138-140, 1994), NOSpA terminator (Jefferson et al., EMBO J 6:3901-7 1987).
Figure 2:
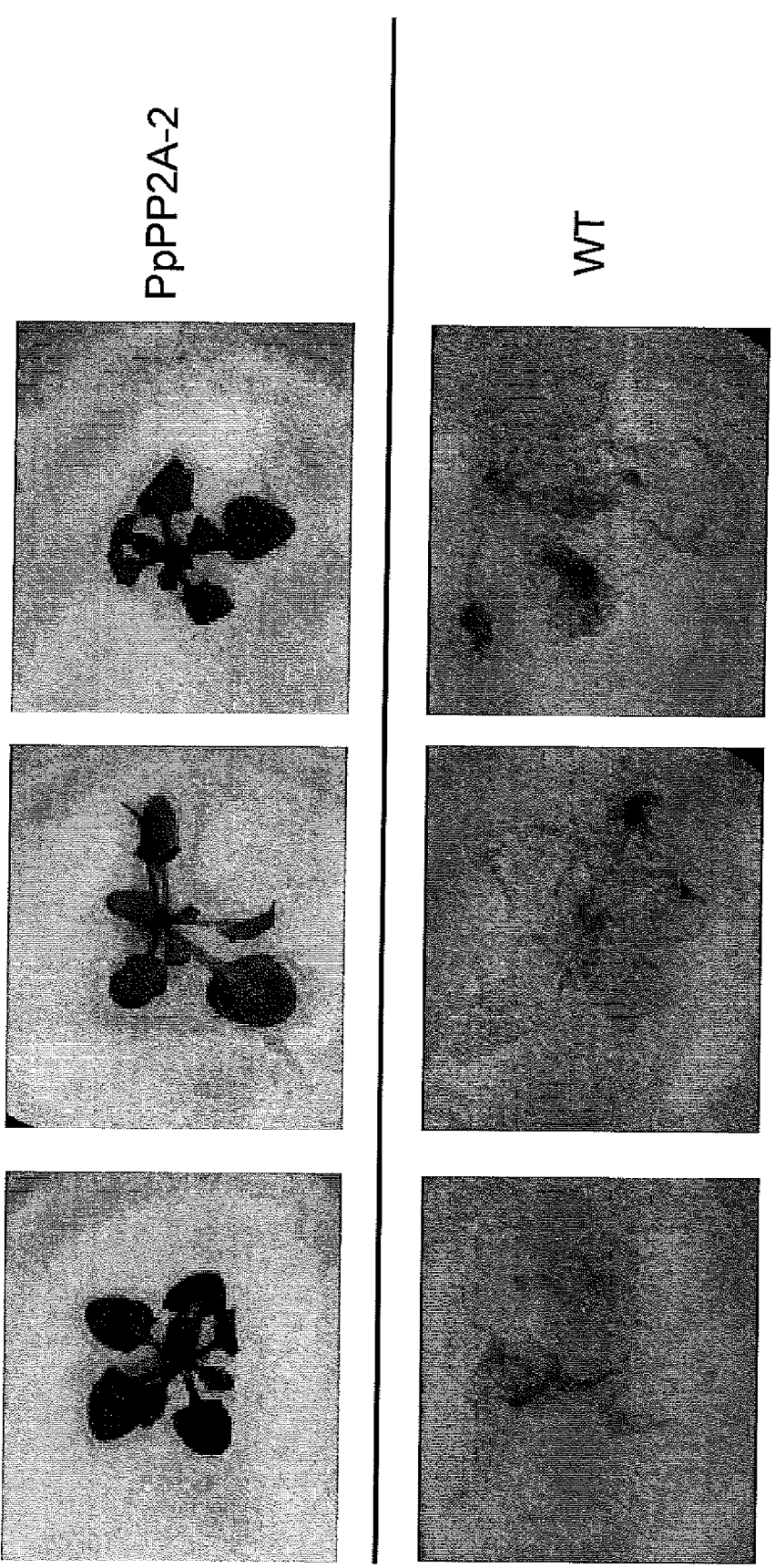
FIG. 2 shows the results of a drought stress test with over-expressing PpPP2A-2 transgenic plants and wild-type *Arabidopsis* lines. The transgenic lines display a tolerant phenotype. Individual transformant lines are shown.
Figure 3:
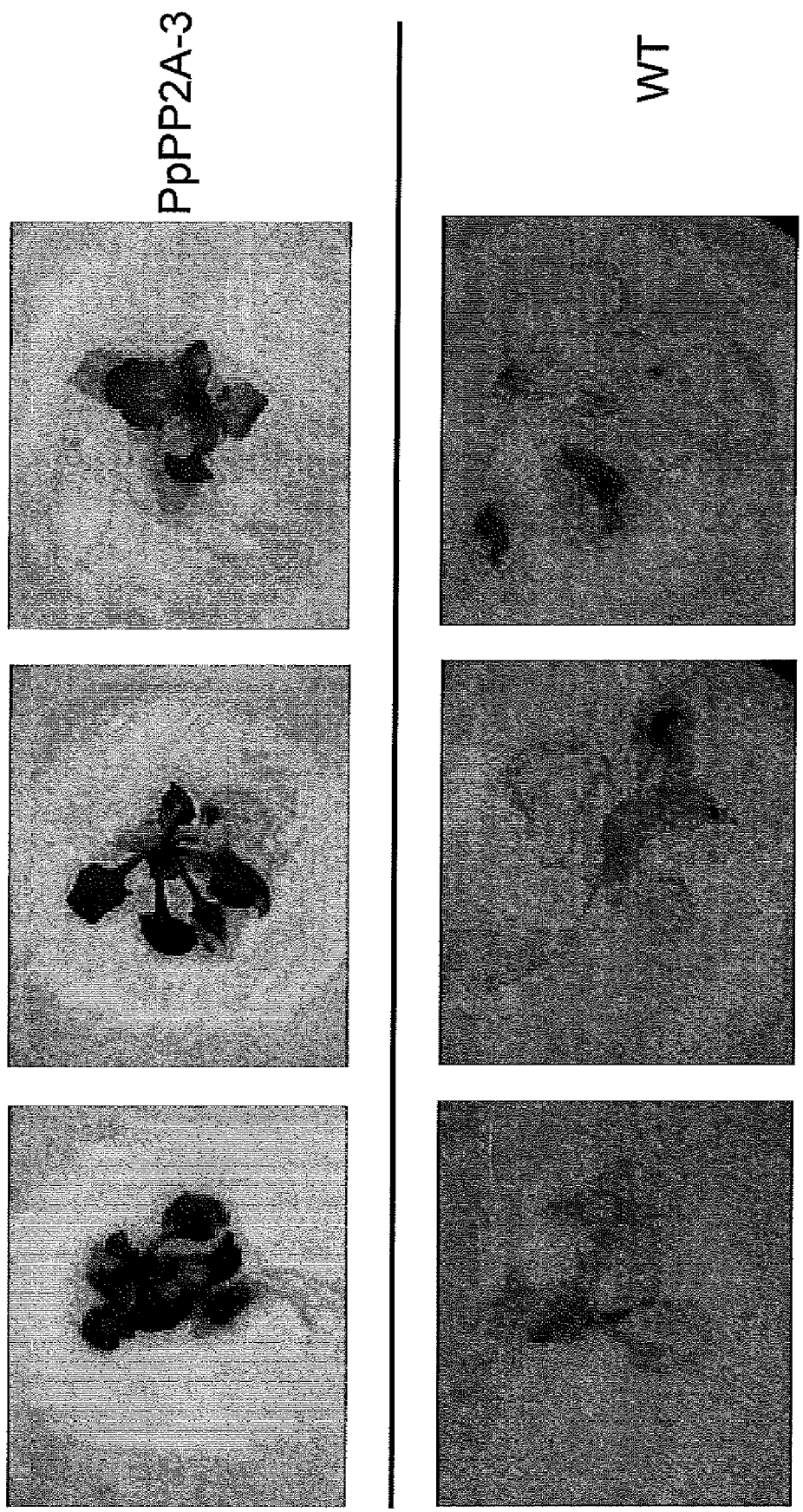
FIG. 3 shows the results of a drought stress test with over-expressing PpPP2A-3 transgenic plants and wild-type *Arabidopsis* lines. The transgenic lines display a tolerant phenotype. Individual transformant lines are shown.
Figure 4:
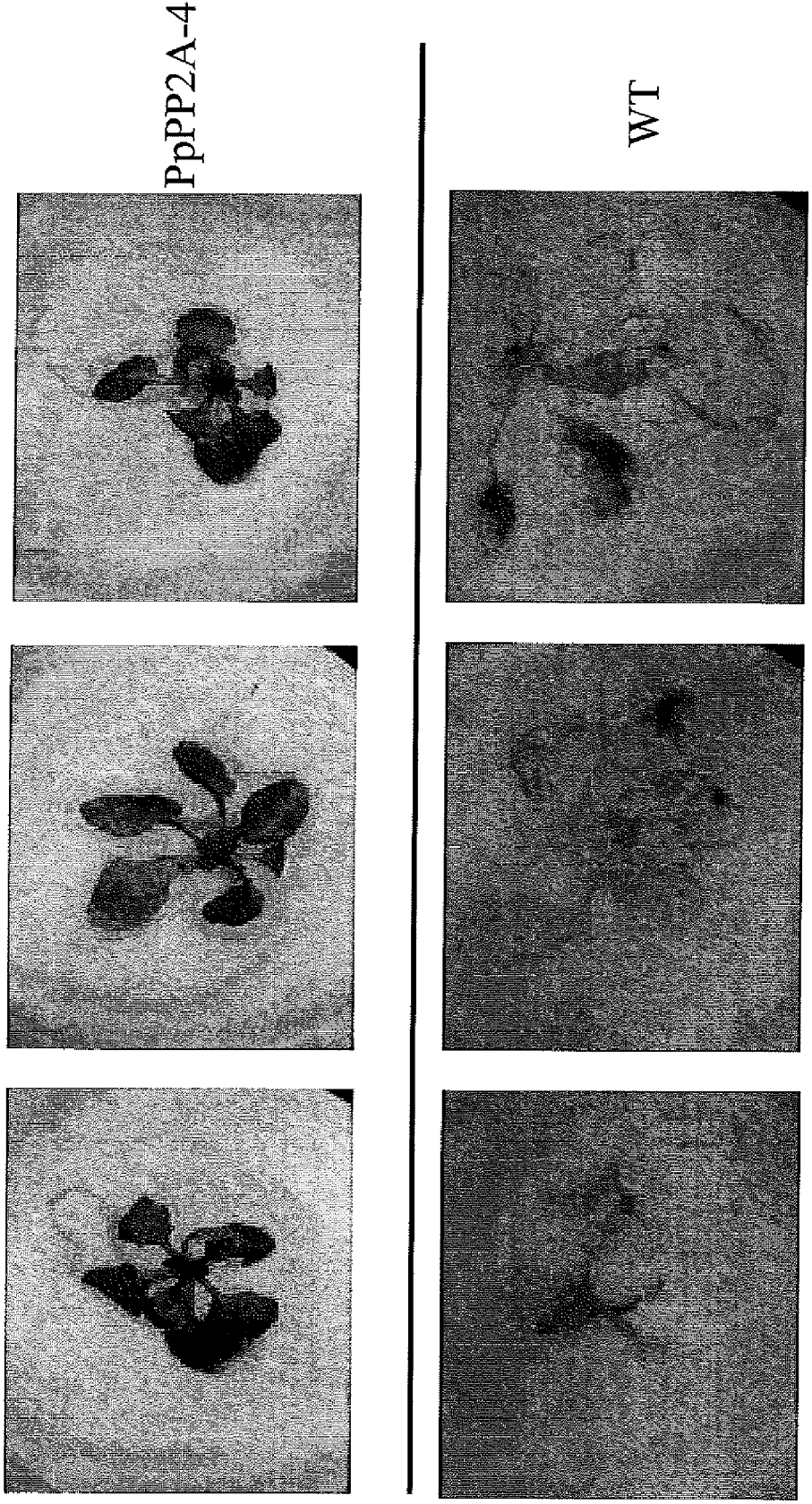
FIG. 4 shows the results of a drought stress test with over-expressing PpPP2A-4 transgenic plants and wild-type *Arabidopsis* lines. The transgenic lines display a tolerant phenotype. Individual transformant lines are shown.
Figure 5:
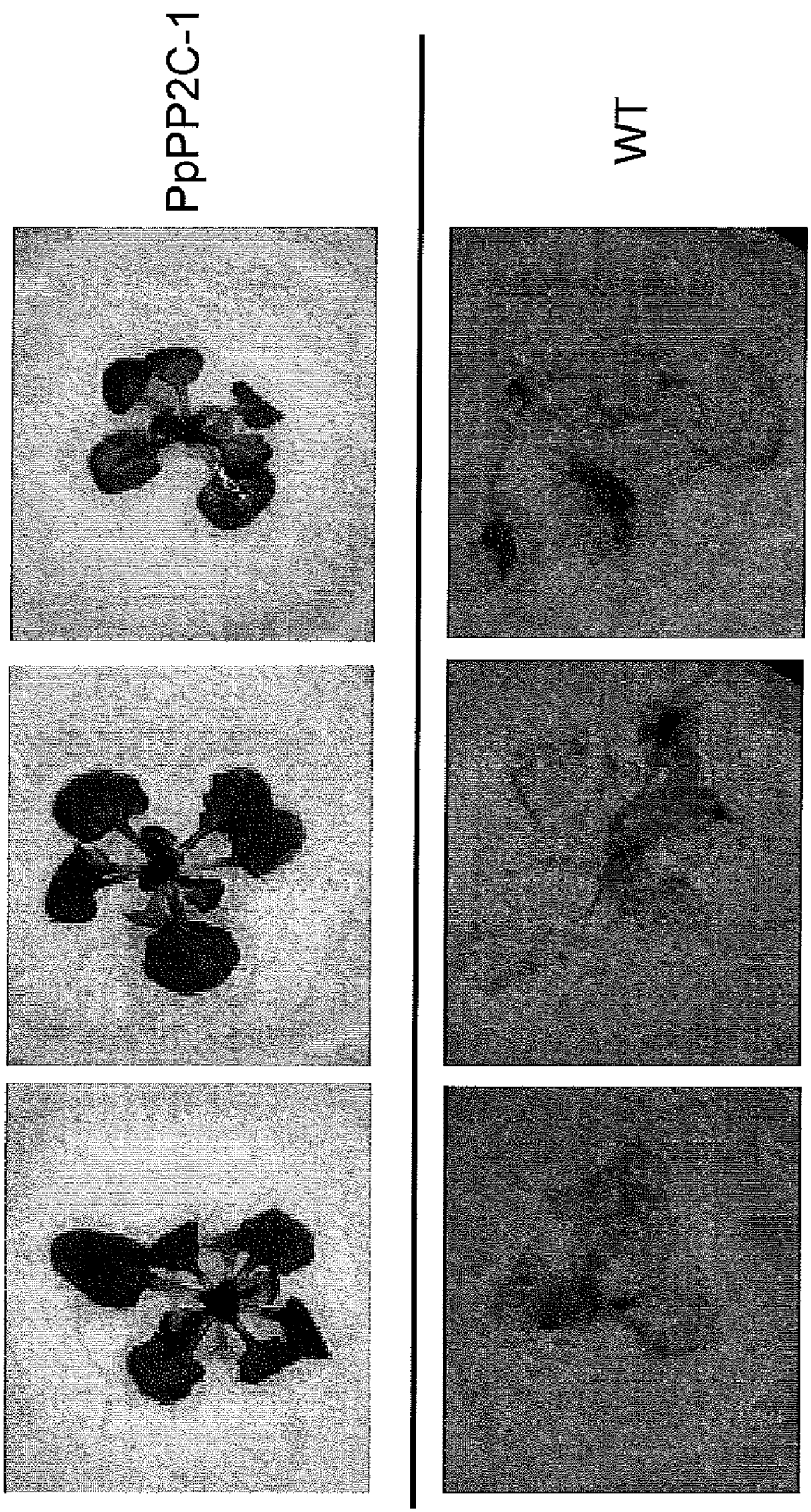
FIG. 5 shows the results of a drought stress test with over-expressing PpPP2C-1 transgenic plants and wild-type *Arabidopsis* lines. The transgenic lines display a tolerant phenotype. Individual transformant lines are shown.
Figure 6:
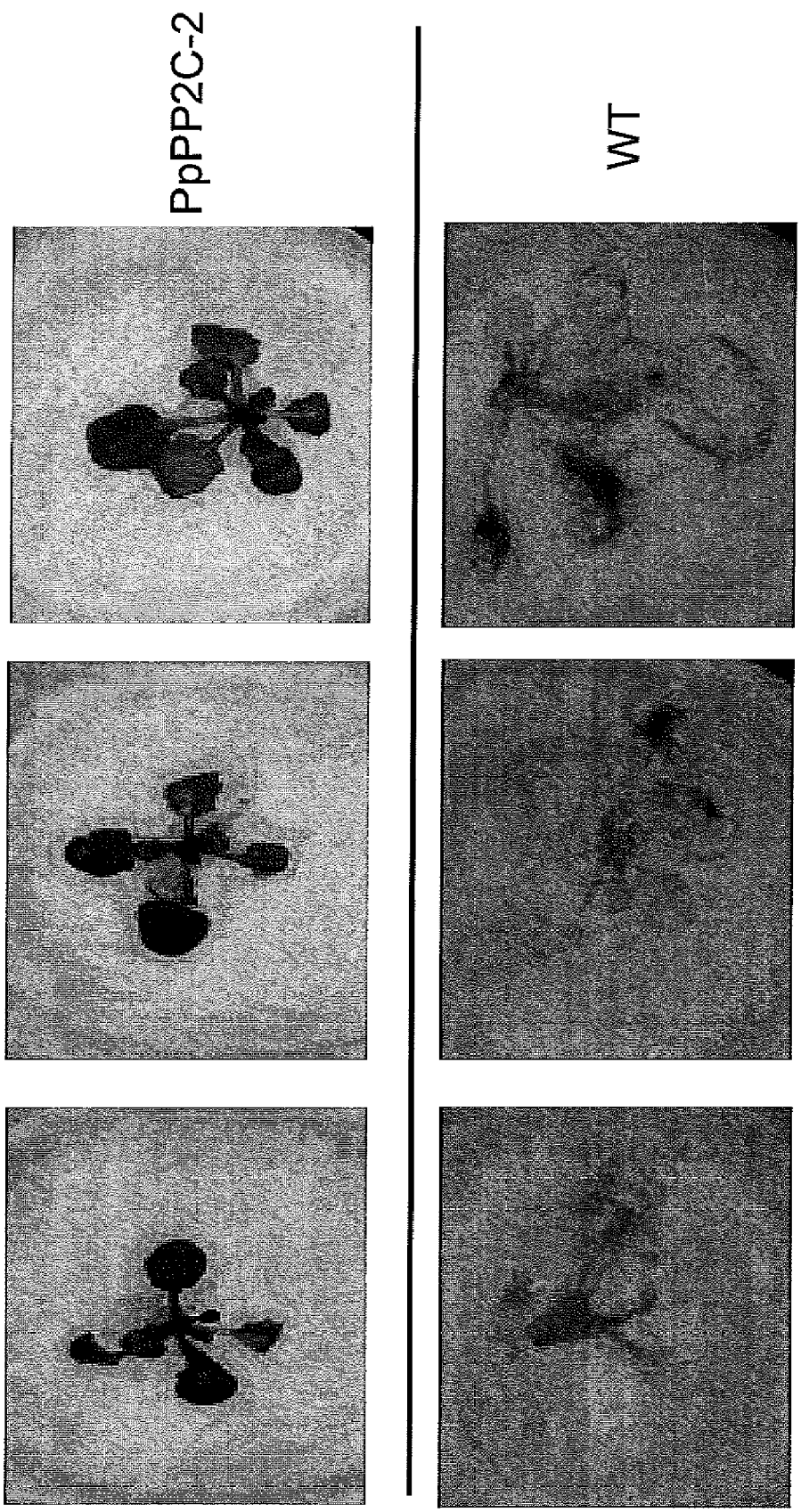
FIG. 6 shows the results of a drought stress test with over-expressing PpPP2C-2 transgenic plants and wild-type *Arabidopsis* lines. The transgenic lines display a tolerant phenotype. Individual transformant lines are shown.
Figure 7:
FIG. 7 shows the results of a freezing stress test with over-expressing PpPP2A-2 transgenic plants and wild-type *Arabidopsis* lines. The transgenic lines display a tolerant phenotype. Individual transformant lines are shown.
Figure 7:
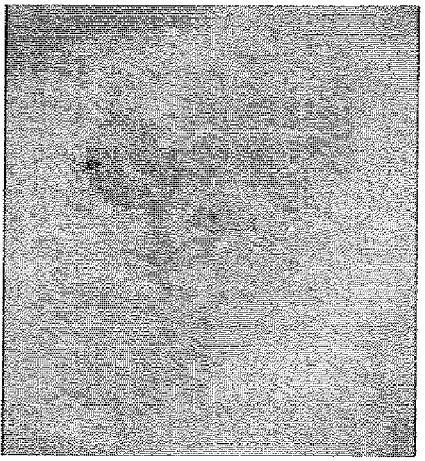
Figure 7:
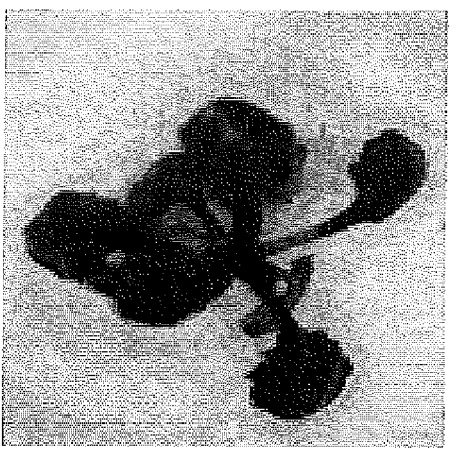
Figure 7:
Figure 7:
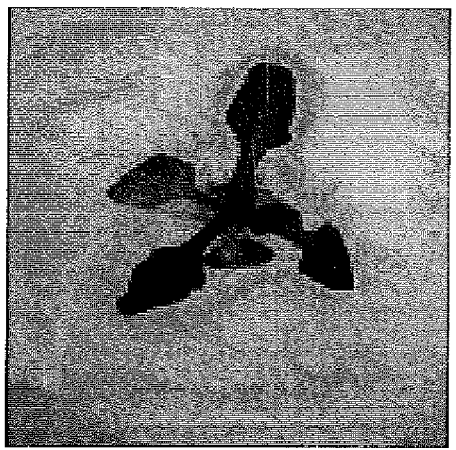
Figure 7:
Figure 8:
FIG. 8 shows the results of a freezing stress test with over-expressing PpPP2A-4 transgenic plants and wild-type *Arabidopsis* lines. The transgenic lines display a tolerant phenotype. Individual transformant lines are shown.
Figure 8:
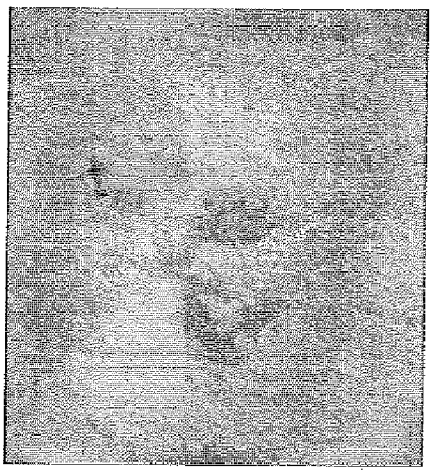
Figure 8:
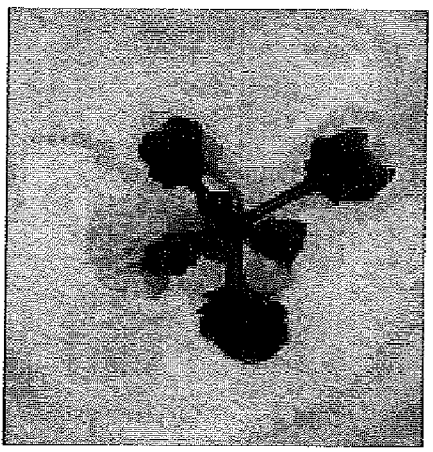
Figure 8:
Figure 8:
Figure 8:
Figure 9:
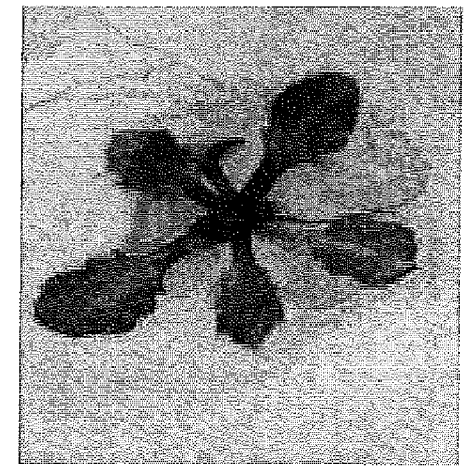
FIG. 9 shows the results of a freezing stress test with over-expressing PpPP2C-1 transgenic plants and wild-type *Arabidopsis* lines. The transgenic lines display a tolerant phenotype. Individual transformant lines are shown.
Figure 9:
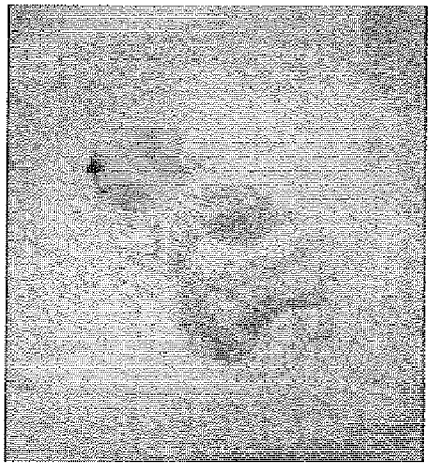
Figure 9:
Figure 9:
Figure 9:
Figure 9:
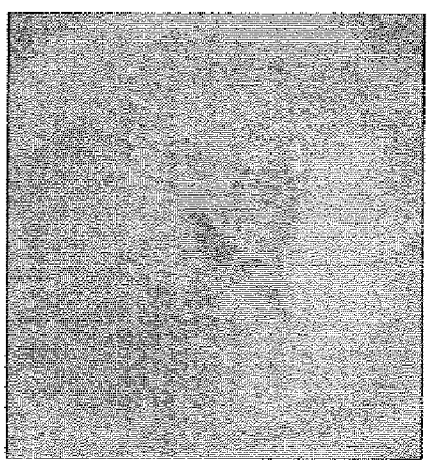
Figure 10:
FIG. 10 shows the results of a freezing stress test with over-expressing PpPP2C-2 transgenic plants and wild-type *Arabidopsis* lines. The transgenic lines display a tolerant phenotype. Individual transformant lines are shown.
Figure 10:
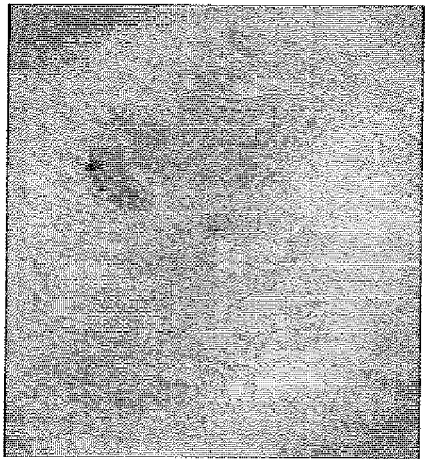
Figure 10:
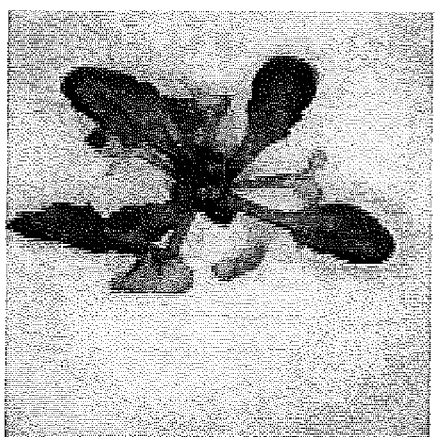
Figure 10:
Figure 10:
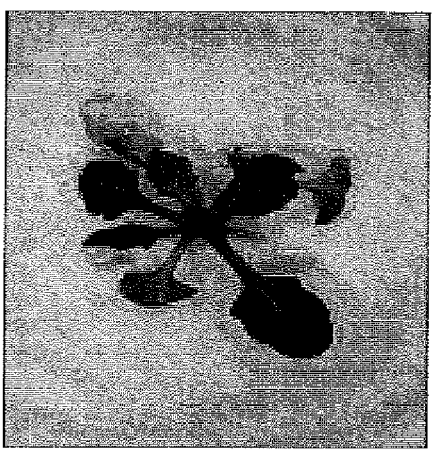
Figure 10:
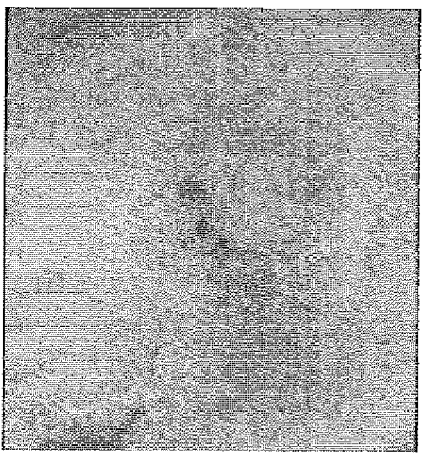

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as protein "PHosphatase Stress-Related Proteins" (PHSRPs), in no way limits the functionality of those sequences.

The present invention provides a transgenic plant cell transformed by a PHSRP coding nucleic acid, wherein expression of the nucleic acid sequence in the plant cell results in increased tolerance to environmental stress as compared to a wild type variety of the plant cell. The invention further provides transgenic plant parts and transgenic plants containing the plant cells described herein. Also provided is a plant seed produced by a transgenic plant transformed by a PHSRP coding nucleic acid, wherein the seed contains the PHSRP coding nucleic acid, and wherein the plant is true breeding for increased tolerance to environmental stress as compared to a wild type variety of the plant. The invention further provides a seed produced by a transgenic plant expressing a PHSRP, wherein the seed contains the PHSRP, and wherein the plant is true breeding for increased tolerance to environmental stress as compared to a wild type variety of the plant. The invention also provides an agricultural product produced by any of the above- or below-described transgenic plants, plant parts and plant seeds.

As used herein, the term "variety" refers to a group of plants within a species that share constant characters that separate them from the typical form and from other possible varieties within that species. While possessing at least one distinctive trait a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* PHSRPs, PP2A-2, PP2A-3, PP2A-4, PP2C-1 and PP2C-2, are useful for increasing a plant's tolerance to environmental stress. The PHSRPs PP2A-2 and PP2A-3 described herein are homologous to the regulatory subunit of protein phosphatase 2A, while PP2A-4 has homology with the catalytic subunit of protein phosphatase 2A as shown in Tables 2, 3 and 4. Additionally, PP2C-1 and PP2C-2 share amino acid sequence similarity with eukaryotic protein phosphatase 2C as shown in Tables 5 and 6. Accordingly, the present invention includes a transgenic plant cell transformed by a PHSRP coding nucleic acid, wherein expression of the nucleic acid sequence in the plant cell results in increased tolerance to an environmental stress as compared to a wild type variety of the plant cell and wherein the PHSRP is a protein phosphatase 2A protein, a protein phosphatase 2C protein, or a homolog or an ortholog thereof.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, or temperature, or combinations thereof and in particular, can be high salinity, low water content or low temperature. It is also to be understood that as used in the specification and in the claims, "a" or "an" can mean one or more, depending upon the context in which it is used. Thus, for example, reference to "a cell" can mean that at least one cell can be utilized.

The invention further describes isolated PHSRPs. In one preferred embodiment, the PHSRPs are isolated from the plant genus *Physcomitrella*. In another preferred embodiment, the PHSRPs are from a *Physcomitrella patens* (*P. patens*) plant. The present invention describes for the first time the predicted *P. patens* proteins PP2A-2 (SEQ ID NO:11), PP2A-3 (SEQ ID NO:12) and PP2A-4 (SEQ ID NO:13) that are homologous to protein phosphatase 2A. Other novel predicted proteins described herein are PP2C-1 (SEQ ID NO:14) and PP2C-2 (SEQ ID NO:15) that are homologous to protein phosphatase 2C. Accordingly, in a preferred embodiment, the PHSRP is a protein phosphatase 2A protein, a protein phosphatase 2C protein or a homolog or an ortholog thereof. In a further preferred embodiment, the PHSRP is selected from the group consisting of PP2A-2 (SEQ ID NO:11), PP2A-3 (SEQ ID NO:12), PP2A-4 (SEQ ID NO:13), PP2C-1 (SEQ ID NO:14), PP2C-2 (SEQ ID NO:15) and homologs and orthologs thereof. Homologs and orthologs of amino acid sequences are defined below.

PHSRPs are preferably produced by recombinant DNA techniques. For example, a nucleic acid molecule encoding the protein is cloned into an expression vector (as described below), the expression vector is introduced into a host cell (as described below) and the PHSRP is expressed in the host cell. The PHSRP can then be isolated from the cells by an appropriate purification scheme using standard protein purification techniques. Alternative to recombinant expression, a PHSRP polypeptide, or peptide can be synthesized chemically using standard peptide synthesis techniques. Moreover, native PHSRP can be isolated from cells (e.g., *Physcomitrella patens*), for example using an anti-PHSRP antibody, which can be produced by standard techniques utilizing a PHSRP or fragment thereof, respectively.

In addition to isolated PHSRPs, the invention provides isolated PHSRP coding nucleic acids. As used herein, the terms "nucleic acid" and "nucleic acid molecule" are intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA.

An "isolated" nucleic acid molecule is one that is substantially separated from other nucleic acid molecules which are present in the natural source of the nucleic acid. Preferably, an "isolated" nucleic acid is free of some of the sequences which naturally flank the nucleic acid (i.e., sequences located at the 5' and 3' ends of the nucleic acid) in the genomic DNA of the organism from which the nucleic acid is derived. For example, in various embodiments, the isolated PHSRP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Physcomitrella patens* cell). Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A nucleic acid molecule of the present invention, e.g., a nucleic acid molecule having a nucleotide sequence of SEQ ID NO:6, SEQ ID NO:7, SEQ ID NO:8, SEQ ID NO:9 or SEQ ID NO:10, or a portion thereof, can be isolated using standard molecular biology techniques and the sequence information provided herein. For example, a *P. patens* PHSRP cDNA can be isolated from a *P. patens* library using all or portion of one of the sequences of SEQ ID NO:1, SEQ ID NO:2, SEQ ID NO:3, SEQ ID NO:4 or SEQ ID NO:5. Moreover, a nucleic acid molecule encompassing all or a portion of one of the sequences of SEQ ID NO:1, SEQ ID NO:2, SEQ ID NO:3, SEQ ID NO:4 and SEQ ID NO:5 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:2, SEQ ID NO:3, SEQ ID NO:4 and SEQ ID NO:5. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a PHSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:6, SEQ ID NO:7, SEQ ID NO:8, SEQ ID NO:9 and SEQ ID NO:10. These cDNAs comprise sequences encoding the PHSRPs (i.e., the "coding region", indicated in Table 1), as well as 5' untranslated sequences and 3' untranslated sequences. It is to be understood that SEQ ID NO:6, SEQ ID NO:7, SEQ ID NO:8, SEQ ID NO:9 and SEQ ID NO:10 comprise both coding regions and 5' and 3' untranslated regions. Alternatively, the nucleic acid molecules of the present invention can comprise only the coding region of any of the sequences in SEQ ID NO:6, SEQ ID NO:7, SEQ ID NO:8, SEQ ID NO:9 or SEQ ID NO:10 or can contain whole genomic fragments isolated from genomic DNA. A coding region of these sequences is indicated as an "ORF position". The present invention also includes PHSRP coding nucleic acids that encode PHSRPs as described herein. Preferred is a PHSRP coding nucleic acid that encodes a PHSRP selected from the group consisting of PP2A-2 (SEQ ID NO:11), PP2A-3 (SEQ ID NO:12), PP2A-4 (SEQ ID NO:13), PP2C-11 (SEQ ID NO:14) and PP2C-2 (SEQ ID NO:15).

Moreover, the nucleic acid molecule of the invention can comprise only a portion of the coding region of one of the sequences in SEQ ID NO:6, SEQ ID NO:7, SEQ ID NO:8, SEQ ID NO:9 and SEQ ID NO:10, for example, a fragment which can be used as a probe or primer or a fragment encoding a biologically active portion of a PHSRP. The nucleotide sequences determined from the cloning of the PHSRP genes from *P. patens* allow for the generation of probes and primers designed for use in identifying and/or cloning PHSRP homologs in other cell types and organisms, as well as PHSRP homologs from other mosses and related species.

Portions of proteins encoded by the PHSRP nucleic acid molecules of the invention are preferably biologically active portions of one of the PHSRPs described herein. As used herein, the term "biologically active portion of" a PHSRP is intended to include a portion, e.g., a domain/motif, of a PHSRP that participates in a stress tolerance response in a plant, has an activity as set forth in Table 1, or participates in the transcription of a protein involved in a stress tolerance response in a plant. To determine whether a PHSRP, or a biologically active portion thereof, can participate in transcription of a protein involved in a stress tolerance response in a plant, a stress analysis of a plant comprising the PHSRP may be performed. Such analysis methods are well known to those skilled in the art, as detailed in Example 7. More specifically, nucleic acid fragments encoding biologically active portions of a PHSRP can be prepared by isolating a portion of one of the sequences in SEQ ID NO:11, SEQ ID NO:12, SEQ ID NO:13, SEQ ID NO:14 and SEQ ID NO:15, expressing the encoded portion of the PHSRP or peptide (e.g., by recombinant expression in vitro) and assessing the activity of the encoded portion of the PHSRP or peptide.

Biologically active portions of a PHSRP are encompassed by the present invention and include peptides comprising amino acid sequences derived from the amino acid sequence of a PHSRP, e.g., an amino acid sequence of SEQ ID NO:11, SEQ ID NO:12, SEQ ID NO:13 SEQ ID NO:14 or SEQ ID NO:15 or the amino acid sequence of a protein homologous or orthologous to a PHSRP, which include fewer amino acids than a full length PHSRP or the full length protein which is homologous or orthologous to a PHSRP, and exhibit at least one activity of a PHSRP. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a PHSRP. Moreover, other biologically active portions in which other regions of the protein are deleted, can be prepared by recombinant techniques and evaluated for one or more of the activities described herein. Preferably, the biologically active portions of a PHSRP include one or more selected domains/motifs or portions thereof having biological activity.

The invention also provides PHSRP chimeric or fusion proteins. As used herein, a PHSRP "chimeric protein" or "fusion protein" comprises a PHSRP polypeptide operatively linked to a non-PHSRP polypeptide. A PHSRP polypeptide refers to a polypeptide having an amino acid sequence corresponding to a PHSRP, whereas a non-PHSRP polypeptide refers to a polypeptide having an amino acid sequence corresponding to a protein which is not substantially homologous to the PHSRP), e.g., a protein that is different from the PHSRP and is derived from the same or a different organism. Within the fusion protein, the term "operatively linked" is intended to indicate that the PHSRP polypeptide and the non-PHSRP polypeptide are fused to each other so that both sequences fulfill the proposed function attributed to the sequence used. The non-PHSRP polypeptide can be fused to the N-terminus or C-terminus of the PHSRP polypeptide. For example, in one embodiment, the fusion protein is a GST-PHSRP fusion protein in which the PHSRP sequences are fused to the C-terminus of the GST sequences. Such fusion proteins can facilitate the purification of recombinant PHSRPs. In another embodiment, the fusion protein is a PHSRP containing a heterologous signal sequence at its N-terminus. In certain host cells (e.g., mammalian host cells), expression and/or secretion of a PHSRP can be increased through use of a heterologous signal sequence.

Preferably, a PHSRP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, Eds. Ausubel et al. John Wiley & Sons: 1992). Moreover, many expression vectors are commercially available that already encode a fusion moiety (e.g., a GST polypeptide). A PHSRP encoding nucleic acid can be cloned into such an expression vector such that the fusion moiety is linked in-frame to the PHSRP.

In addition to fragments and fusion proteins of the PHSRPs described herein, the present invention includes homologs and analogs of naturally occurring PHSRPs and PHSRP encoding nucleic acids in a plant. "Homologs" are defined herein as two nucleic acids or proteins that have similar, or "homologous", nucleotide or amino acid sequences, respectively, Homologs include allelic variants, orthologs, paralogs, agonists and antagonists of PHSRPs as defined hereafter. The term "homolog" further encompasses nucleic acid molecules that differ from one of the nucleotide sequences shown in SEQ ID NO:6, SEQ ID NO:7, SEQ ID NO:8, SEQ ID NO:9 or SEQ ID NO:10 (and portions thereof) due to degeneracy of the genetic code and thus encode the same PHSRP as that encoded by the nucleotide sequences shown in SEQ ID NO:6, SEQ ID NO:7, SEQ ID NO:8, SEQ ID NO:9 or SEQ ID NO:10.

An agonist of the PHSRP can retain substantially the same, or a subset, of the biological activities of the PHSRP. An antagonist of the PHSRP can inhibit one or more of the activities of the naturally occurring form of the PHSRP. For example, the PHSRP antagonist can competitively bind to a downstream or upstream member of the cell membrane component metabolic cascade that includes the PHSRP, or bind to a PHSRP that mediates transport of compounds across such membranes, thereby preventing translocation from taking place.

As used herein a "naturally occurring" PHSRP refers to a PHSRP amino acid sequence that occurs in nature. Preferably, a naturally occurring PHSRP comprises an amino acid sequence selected from the group consisting of SEQ ID NO:11, SEQ ID NO:12, SEQ ID NO:13, SEQ ID NO:14 and SEQ ID NO:15.

Nucleic acid molecules corresponding to natural allelic variants and analogs, orthologs and paralogs of a PHSRP cDNA can be isolated based on their identity to the *Physcomitrella patens* PHSRP nucleic acids described herein using PHSRP cDNAs, respectively, or a portion thereof, as a hybridization probe according to standard hybridization techniques under stringent hybridization conditions. In an alternative embodiment, homologs of the PHSRP can be identified by screening combinatorial libraries of mutants, e.g., truncation mutants, of the PHSRP for PHSRP agonist or antagonist activity. In one embodiment, a variegated library of PHSRP variants is generated by combinatorial mutagenesis at the nucleic acid level and is encoded by a variegated gene library. A variegated library of PHSRP variants can be produced by, for example, enzymatically ligating a mixture of synthetic oligonucleotides into gene sequences such that a degenerate set of potential PHSRP sequences is expressible as individual polypeptides, or alternatively, as a set of larger fusion proteins (e.g., for phage display) containing the set of PHSRP sequences therein. There are a variety of methods that can be used to produce libraries of potential PHSRP homologs from a degenerate oligonucleotide sequence. Chemical synthesis of a degenerate gene sequence can be, performed in an automatic DNA synthesizer, and the synthetic gene is then ligated into an appropriate expression vector. Use of a degenerate set of genes allows for the provision, in one mixture of all of the sequences encoding the desired set of potential PHSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477).

In addition, libraries of fragments of the PHSRP coding regions can be used to generate a variegated population of PHSRP fragments for screening and subsequent selection of homologs of a PHSRP. In one embodiment, a library of coding sequence fragments can be generated by treating a double stranded PCR fragment of a PHSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PHSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PHSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify PHSRP homologs (Arkin and Yourvan, 1992 PNAS 89:7811-7815; Delgrave et al., 1993 Protein Engineering 6(3):327-331). In another embodiment, cell based assays can be exploited to analyze a variegated PHSRP library, using methods well known in the art. The present invention further provides a method of identifying a novel PHSRP, comprising (a) raising a specific antibody response to a PHSRP, or a fragment thereof, as described above; (b) screening putative PHSRP material with the antibody, wherein specific binding of the antibody to the material indicates the presence of a potentially novel PHSRP; and (c) analyzing the bound material in comparison to known PHSRP, to determine its novelty.

To determine the percent homology of two amino acid sequences (e.g., one of the sequences of SEQ ID NO:11, SEQ ID NO:12, SEQ ID NO:13, SEQ ID NO:14 and SEQ ID NO:15 and a mutant form thereof), the sequences are aligned for optimal comparison purposes (e.g., gaps can be introduced in the sequence of one protein or nucleic acid for optimal alignment with the other protein or nucleic acid). The amino acid residues at corresponding amino acid positions or nucleotide positions are then compared. When a position in one sequence (e.g., one of the sequences of SEQ ID NO:11, SEQ ID NO:12, SEQ ID NO:13, SEQ ID NO:14 and SEQ ID NO:15) is occupied by the same amino acid residue as the corresponding position in the other sequence (e.g., a mutant form of the sequence selected from the polypeptide of SEQ ID NO:11, SEQ ID NO:12, SEQ ID NO:13, SEQ ID NO:14 and SEQ ID NO:15), then the molecules are homologous at that position (i.e., as used herein amino acid or nucleic acid "homology" is equivalent to amino acid or nucleic acid "identity"). The same type of comparison can be made between two nucleic acid sequences.

The percent homology between the two sequences is a function of the number of identical positions shared by the sequences (i.e., % homology=numbers of identical positions/total numbers of positions×100). Preferably, the amino acid sequences included in the present invention are at least about 50-60%, preferably at least about 60-70%, and more preferably at least about 70-80%, 80-90%, 90-95%, and most preferably at least about 96%, 97%, 98%, 99% or more homologous to an entire amino acid sequence shown in SEQ ID NO:11, SEQ ID NO:12, SEQ ID NO:13, SEQ ID NO:14 or SEQ ID NO:15. In yet another embodiment, at least about 50-60%, preferably at least about 60-70%, and more preferably at least about 70-80%, 80-90%, 90-95%, and most preferably at least about 96%, 97%, 98%, 99% or more homologous to an entire amino acid sequence encoded by a nucleic acid sequence shown in SEQ ID NO:6, SEQ ID NO:7, SEQ ID NO:8, SEQ ID NO:9 or SEQ ID NO:10. In other embodiments, the preferable length of sequence comparison for proteins is at least 15 amino acid residues, more preferably at least 25 amino acid residues, and most preferably at least 35 amino acid residues.

In another preferred embodiment, an isolated nucleic acid molecule of the invention comprises a nucleotide sequence which is at least about 50-60%, preferably at least about 60-70%, more preferably at least about 70-80%, 80-90%, or 90-95%, and even more preferably at least about 95%, 96%, 97%, 98%, 99% or more homologous to a nucleotide sequence shown in SEQ ID NO:6, SEQ ID NO:7, SEQ ID NO:8, SEQ ID NO:9 or SEQ ID NO:10, or a portion thereof. The preferable length of sequence comparison for nucleic acids is at least 75 nucleotides, more preferably at least 100 nucleotides and most preferably the entire length of the coding region.

It is also preferable that a homologous nucleic acid molecule of the invention encodes a protein, or portion thereof, which includes an amino acid sequence which is sufficiently homologous to an amino acid sequence of SEQ ID NO:11, SEQ ID NO:12, SEQ ID NO:13, SEQ ID NO:14 or SEQ ID NO:15 such that the protein or portion thereof maintains the same or a similar function as the amino acid sequence to which it is compared. Functions of the PHSRP amino acid sequences of the present invention include the ability to participate in a stress tolerance response in a plant, or more particularly, to participate in the transcription of a protein involved in a stress tolerance response in a *Physcomitrella patens* plant. Examples of such activities are described in Table 1.

In addition to the above described methods, a determination of the percent homology between two sequences can be accomplished using a mathematical algorithm. A preferred, non-limiting example of a mathematical algorithm utilized for the comparison of two sequences is the algorithm of Karlin and Altschul (1990 Proc. Natl. Acad. Sci. USA 90:5873-5877). Such an algorithm is incorporated into the NBLAST and XBLAST programs of Altschul, et al. (1990 J. Mol. Biol. 215:403-410).

BLAST nucleic acid searches can be performed with the NBLAST program, score=100, wordlength=12 to obtain nucleic acid sequences homologous to the PHSRP nucleic acid molecules of the invention. Additionally, BLAST protein searches can be performed with the XBLAST program, score=50, wordlength=3 to obtain amino acid sequences homologous to PHSRPs of the present invention. To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used to obtain amino acid sequences homologous to the PHSRPs of the present invention. To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used.

Finally, homology between nucleic acid sequences can also be determined using hybridization techniques known to those of skill in the art. Accordingly, an isolated nucleic acid molecule of the invention comprises a nucleotide sequence which hybridizes, e.g., hybridizes under stringent conditions, to one of the nucleotide sequences shown in SEQ ID NO:6, SEQ ID NO:7, SEQ ID NO:8, SEQ ID NO:9 or SEQ ID NO:10 or a portion thereof. More particularly, an isolated nucleic acid molecule of the invention is at least 15 nucleotides in length and hybridizes under stringent conditions to the nucleic acid molecule comprising a nucleotide sequence of SEQ ID NO:6, SEQ ID NO:7, SEQ ID NO:8, SEQ ID NO:9 or SEQ ID NO:10. In other embodiments, the nucleic acid is at least 30, 50, 100, 250 or more nucleotides in length.

As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, 6.3.1-6.3.6, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a sequence of SEQ ID NO:6, SEQ ID NO:7, SEQ ID NO:8, SEQ ID NO:9 or SEQ ID NO:10 corresponds to a naturally occurring nucleic acid molecule. As used herein, a "naturally occurring" nucleic acid molecule refers to an RNA or DNA molecule having a nucleotide sequence that occurs in nature (e.g., encodes a natural protein). In one embodiment, the nucleic acid encodes a naturally occurring *Physcomitrella patens* PHSRP.

Using the above-described methods, and others known to those of skill in the art, one of ordinary skill in the art can isolate homologs of the PHSRPs comprising amino acid sequences shown in SEQ ID NO:11, SEQ ID NO:12, SEQ ID NO:13, SEQ ID NO:14 or SEQ ID NO:15 and the PHSRP nucleic acids comprising nucleic acid sequences as shown in SEQ ID NO:6, SEQ ID NO:7, SEQ ID NO:8, SEQ ID NO:9 or SEQ ID NO:10. One subset of these homologs are allelic variants. As used herein, the term "allelic variant" refers to a nucleotide sequence containing polymorphisms that lead to changes in the amino acid sequences of a PHSRP and that exist within a natural population (e.g., a plant species or variety). Such natural allelic variations can typically result in 1-5% variance in a PHSRP nucleic acid. Allelic variants can be identified by sequencing the nucleic acid sequence of interest in a number of different plants, which can be readily carried out by using hybridization probes to identify the same PHSRP genetic locus in those plants. Any and all such nucleic acid variations and resulting amino acid polymorphisms or variations in a PHSRP that are the result of natural allelic variation and that do not alter the functional activity of a PHSRP, are intended to be within the scope of the invention.

Moreover, nucleic acid molecules encoding PHSRPs from the same or other species such as PHSRP analogs, orthologs and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode proteins having the same or similar functions. As also used herein, the term "paralogs" refers to two nucleic acids that are related by duplication within a genome. Paralogs usually have different functions, but these functions may be related (Tatusov, R. L. et al. 1997 Science 278(5338):631-637). Analogs, orthologs and paralogs of a naturally occurring PHSRP can differ from the naturally occurring PHSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably 90%, and most preferably 95%, 96%, 97%, 98% or even 99% identity or homology with all or part of a naturally occurring PHSRP amino acid sequence and will exhibit a function similar to a PHSRP. Orthologs of the present invention are also preferably capable of participating in the stress response in plants. In one embodiment, the PHSRP orthologs maintain the ability to participate in the metabolism of compounds necessary for the construction of cellular membranes in *Physcomitrella patens*, or in the transport of molecules across these membranes.

In addition to naturally-occurring variants of a PHSRP sequence that may exist in the population, the skilled artisan will further appreciate that changes can be introduced by mutation into a nucleotide sequence of SEQ ID NO:6, SEQ ID NO:7, SEQ ID NO:8, SEQ ID NO:9 or SEQ ID NO:10, thereby leading to changes in the amino acid sequence of the encoded PHSRP, without altering the functional ability of the PHSRP. For example, nucleotide substitutions leading to amino acid substitutions at "non-essential" amino acid residues can be made in a sequence of SEQ ID NO:6, SEQ ID NO:7, SEQ ID NO:8, SEQ ID NO:9 or SEQ ID NO:10. A "non-essential" amino acid residue is a residue that can be altered from the wild-type sequence of one of the PHSRPs without altering the activity of said PHSRP, whereas an "essential" amino acid residue is required for PHSRP activity. Other amino acid residues, however, (e.g., those that are not conserved or only semi-conserved in the domain having PHSRP activity) may not be essential for activity and thus are likely to be amenable to alteration without altering PHSRP activity.

Accordingly, another aspect of the invention pertains to nucleic acid molecules encoding PHSRPs that contain changes in amino acid residues that are not essential for PHSRP activity. Such PHSRPs differ in amino acid sequence from a sequence contained in SEQ ID NO:11, SEQ ID NO:12, SEQ ID NO:13, SEQ ID NO:14 or SEQ ID NO:15, yet retain at least one of the PHSRP activities described herein. In one embodiment, the isolated nucleic acid molecule comprises a nucleotide sequence encoding a protein, wherein the protein comprises an amino acid sequence at least about 50% homologous to an amino acid sequence of SEQ ID NO:11, SEQ ID NO:12, SEQ ID NO:13, SEQ ID NO:14 or SEQ ID NO:15. Preferably, the protein encoded by the nucleic acid molecule is at least about 50-60% homologous to one of the sequences of SEQ ID NO:11, SEQ ID NO:12, SEQ ID NO:13, SEQ ID NO:14 or SEQ ID NO:15, more preferably at least about 60-70% homologous to one of the sequences of SEQ ID NO:1, SEQ ID NO:12, SEQ ID NO:13, SEQ ID NO:14 or SEQ ID NO:15, even more preferably at least about 70-80%, 80-90%, 90-95% homologous to one (of the sequences of SEQ ID NO:1, SEQ ID NO:12, SEQ ID NO:13, SEQ ID NO:14 or SEQ ID NO:15, and most preferably at least about 96%, 97%, 98%, or 99% homologous to one of the sequences of SEQ ID NO:1, SEQ ID NO:12, SEQ ID NO:13, SEQ ID NO:14 or SEQ ID NO:15. The preferred PHSRP homologs of the present invention are preferably capable of participating in the stress tolerance response in a plant, or more particularly, participating in the transcription of a protein involved in a stress tolerance response in a *Physcomitrella patens* plant, or have one or more activities set forth in Table 1.

An isolated nucleic acid molecule encoding a PHSRP homologous to a protein sequence of SEQ ID NO:11, SEQ ID NO:12, SEQ ID NO:13, SEQ ID NO:14 or SEQ ID NO:15 can be created by introducing one or more nucleotide substitutions, additions or deletions into a nucleotide sequence of SEQ ID NO:6, SEQ ID NO:7, SEQ ID NO:8, SEQ ID NO:9 or SEQ ID NO:10 such that one or more amino acid substitutions, additions or deletions are introduced into the encoded protein. Mutations can be introduced into one of the sequences of SEQ ID NO:6, SEQ ID NO:7, SEQ ID NO:8, SEQ ID NO:9 and SEQ ID NO:10 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PHSRP is preferably replaced with another amino acid residue from the same side chain family. Alternatively, in another embodiment, mutations can be introduced randomly along all or part of a PHSRP coding sequence, such as by saturation mutagenesis, and the resultant mutants can be screened for a PHSRP activity described herein to identify mutants that retain PHSRP activity. Following mutagenesis of one of the sequences of SEQ ID NO:6, SEQ ID NO:7, SEQ ID NO:8, SEQ ID NO:9 and SEQ ID NO:10, the encoded protein can be expressed recombinantly and the activity of the protein can be determined by analyzing the stress tolerance of a plant expressing the protein as described in Example 7.

In addition to the nucleic acid molecules encoding the PHSRPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PHSRP coding strand, or to only a portion thereof. In one embodiment, an antisense nucleic acid molecule is antisense to a "coding region" of the coding strand of a nucleotide sequence encoding a PHSRP. The term "coding region" refers to the region of the nucleotide sequence comprising codons that are translated into amino acid residues (e.g., the entire coding region of, comprises nucleotides 1 to . . . ). In another embodiment, the antisense nucleic acid molecule is antisense to a "noncoding region" of the coding strand of a nucleotide sequence encoding a PHSRP. The term "noncoding region" refers to 5' and 3' sequences that flank the coding region that are not translated into amino acids (i.e., also referred to as 5' and 3' untranslated regions).

In a preferred embodiment, an isolated nucleic acid molecule of the invention comprises a nucleic acid molecule which is a complement of one of the nucleotide sequences shown in SEQ ID NO:6, SEQ ID NO:7, SEQ ID NO:8, SEQ ID NO:9 and SEQ ID NO:10, or a portion thereof. A nucleic acid molecule that is complementary to one of the nucleotide sequences shown in SEQ ID NO:6, SEQ ID NO:7, SEQ ID NO:8, SEQ ID NO:9 and SEQ ID NO:10 is one which is sufficiently complementary to one of the nucleotide sequences shown in SEQ ID NO:6, SEQ ID NO:7, SEQ ID NO:8, SEQ ID NO:9 and SEQ ID NO:10 such that it can hybridize to one of the nucleotide sequences shown in SEQ ID NO:6, SEQ ID NO:7, SEQ ID NO:8, SEQ ID NO:9 and SEQ ID NO:10, thereby forming a stable duplex.

Given the coding strand sequences encoding the PHSRPs disclosed herein (e.g., the sequences set forth in SEQ ID NO:6, SEQ ID NO:7, SEQ ID NO:8, SEQ ID NO:9 and SEQ ID NO:10), antisense nucleic acids of the invention can be designed according to the rules of Watson and Crick base pairing. The antisense nucleic acid molecule can be complementary to the entire coding region of a PHSRP mRNA, but more preferably is an oligonucleotide which is antisense to only a portion of the coding or noncoding region of a PHSRP in RNA. For example, the antisense oligonucleotide can be complementary to the region surrounding the translation start site of PHSRP mRNA. An antisense oligonucleotide can be, for example, about 5, 10, 15, 20, 25, 30, 35, 40, 45 or 50 nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a PHSRP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625-6641). The antisense nucleic acid molecule can also comprise a 2'-o-methylribonucleotide (Inoue et al., 1987 Nucleic Acids Res. 15:6131-6148) or a chimeric RNA-DNA analogue (Inoue et al., 1987 FEBS Lett. 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes described in Haselhoff and Gerlach, 1988 Nature 334:585-591) can be used to catalytically cleave PHSRP mRNA transcripts to thereby inhibit translation of PHSRP mRNA. A ribozyme having specificity for a PHSRP-encoding nucleic acid can be designed based upon the nucleotide sequence of a PHSRP cDNA, as disclosed herein (i.e., SEQ ID NO:6, SEQ ID NO:7, SEQ ID NO:8, SEQ ID NO:9 or SEQ ID NO:10) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a PHSRP-encoding V RNA. See, e.g., Cech et al. U.S. Pat. No. 4,987,071 and Cech et al. U.S. Pat. No. 5,116,742. Alternatively, PHSRP mRNA can be used to select a catalytic RNA having a specific ribonuclease activity from a pool of RNA molecules. (See, e.g., Bartel, D. and Szostak, J. W., 1993 Science 261:1411-1418).

Alternatively, PHSRP gene expression can be inhibited by targeting nucleotide sequences complementary to the regulatory region of a PHSRP nucleotide sequence (e.g., a PHSRP promoter and/or enhancer) to form triple helical structures that prevent transcription of a PHSRP gene in target cells. See generally, Helene, C., 1991 Anticancer Drug Des. 6(6):569-84; Helene, C. et al., 1992 Ann. N.Y. Acad. Sci. 660:27-36; and Maher, L. J., 1992 Bioassays 14(12):807-15.

In addition to the PHSRP nucleic acids and proteins described above, the present invention encompasses these nucleic acids and proteins attached to a moiety. These moieties include, but are not limited to, detection moieties, hybridization moieties, purification moieties, delivery moieties, reaction moieties, binding moieties, and the like. One typical nucleic acid bound to a moiety is a probe/primer. The probe/primer typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:6, SEQ ID NO:7, SEQ ID NO:8, SEQ ID NO:9 and SEQ ID NO:10, an anti-sense sequence of one of the sequences set forth in SEQ ID NO:6, SEQ ID NO:7, SEQ ID NO:8, SEQ ID NO:9 and SEQ ID NO:10, or naturally occurring mutants thereof. Primers based on a nucleotide sequence of SEQ ID NO:6, SEQ ID NO:7, SEQ ID NO:8, SEQ ID NO:9 or SEQ ID NO:10 can be used in PCR reactions to clone PHSRP homologs. Probes based on the PHSRP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a PHSRP, such as by measuring a level of a PHSRP-encoding nucleic acid, respectively, in a sample of cells, e.g., detecting PHSRP mRNA levels or determining whether a genomic PHSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: New York). This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317-326. To assess the presence or relative quantity of protein translated from this mRNA, standard techniques, such as a Western blot, may be employed. These techniques are well known to one of ordinary skill in the art. (See, for example, Ausubel et al., 1988 Current Protocols in Molecular Biology, Wiley: New York).

The invention further provides an isolated recombinant expression vector comprising a PHSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequencers) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or tinder certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PHSRPs, mutant forms of PHSRPs, fusion proteins, etc.).

The recombinant expression vectors of the invention can be designed for expression of PHSRPs in prokaryotic or eukaryotic cells. For example, PHSRP genes can be expressed in bacterial cells such as *C. glutamicum*, insect cells (using baculovirus expression vectors), yeast and other fungal cells (see Romanos, M. A. et al., 1992 Foreign gene expression in yeast: a review, Yeast 8:423-488; van den Hondel, C. A. M. J. J. et al., 1991 Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J., 1991 Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999 Marine Biotechnology 1(3):239-251), ciliates of the types: *Holotrichia*, Peritrichia, Spirotrichia, Suctoria, *Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in WO 98/01572 and multicellular plant cells (see Schmidt, R. and Willmitzer, L., 1988 High efficiency *Agrobacterium tumefaciens*-mediated transformation of *Arabidopsis thaliana* leaf and cotyledon explants, Plant Cell Rep. 583-586); Plant Molecular Biology and Biotechnology, C Press, Boca Raton, Fla., chapter 6/7, S.71-119 (1993); F. F. White, B. Jenes et al., Techniques for Gene Transfer, in: Transgenic Plants, Vol. 1, Engineering and Utilization, eds. Kung und R. Wu, 128-43, Academic Press: 1993; Potrykus, 1991 Annu. Rev. Plant Physiol. Plant Molec. Biol. 42:205-225 and references cited therein) or mammalian cells. Suitable host cells are discussed further in Goeddel, *Gene Expression Technology: Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of a recombinant protein; 2) to increase the solubility of a recombinant protein; and 3) to aid in the purification of a recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S., 1988 Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the PHSRP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant PHSRP unfused to GST can be recovered by cleavage of the fusion protein with thrombin.

Examples of suitable inducible non-fusion *E. coli* expression vectors include pTrc (Amann et al., 1988 Gene 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter Target gene expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174 (DE3) from a resident X prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992 Nucleic Acids Res. 20:2111-2118). Such alteration of nucleic acid sequences of the invention can be carried out by standard DNA synthesis techniques.

In another embodiment, the PHSRP expression vector is a yeast expression vector. Examples of vectors for expression in yeast *S. cerevisiae* include pYepSec1 (Baldari, et al., 1987 Embo J. 6:229-234), pMFa (Kurjan and Herskowitz, 1982 Cell 30:933-943), pJRY88 (Schultz et al., 1987 Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge.

Alternatively, the PHSRPs of the invention can be expressed in insect cells using baculovirus expression vectors. Baculovirus vectors available for expression of proteins in cultured insect cells (e.g., Sf 9 cells) include the pAc series (Smith et al., 1983 Mol. Cell. Biol. 3:2156-2165) and the pVL series (Lucklow and Summers, 1989 Virology 170:31-39).

In yet another embodiment, a PHSRP nucleic acid of the invention is expressed in mammalian cells using a mammalian expression vector. Examples of mammalian expression vectors include pCDM8 (Seed, B., 1987 Nature 329:840) and pMT2PC (Kaufman et al., 1987 EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual*. $2^{nd}$, ed., *Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987 Genes Dev. 1:268-277), lymphoid-specific promoters (Calame and Eaton, 1988 Adv. Immunol. 43:235-275), in particular promoters of T cell receptors (Winoto and Baltimore, 1989 EMBO J. 8:729-733) and immunoglobulins (Banerji et al., 1983 Cell 33:729-740; Queen and Baltimore, 1983 Cell 33:741-748), neuron-specific promoters (e.g., the neurofilament promoter; Byrne and Ruddle, 1989 *PNAS* 86:5473-5477), pancreas-specific promoters (Edlund et al., 1985 Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, 1990 Science 249:374-379) and the fetoprotein promoter (Campes and Tilghman, 1989 Genes Dev. 3:537-546).

In another embodiment, the PHSRPs of the invention may be expressed in unicellular plant cells (such as algae) (see Falciatore et al., 1999 Marine Biotechnology 1(3):239-251 and references therein) and plant cells from higher plants (e.g., the spermatophytes, such as crop plants). Examples of plant expression vectors include those detailed in: Becker, D., Kemper; E., Schell, J. and Masterson, R., 1992 New plant binary vectors with selectable markers located proximal to the left border, Plant Mol. Biol. 20: 1195-1197; and Bevan, M. W., 1984 Binary *Agrobacterium* vectors for plant transformation, Nucl. Acid. Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38.

A plant expression cassette preferably contains regulatory sequences capable of driving gene expression in plant cells and operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., 1987 Nucl, Acids Research 15:8693-8711).

Plant gene expression has to be operably linked to an appropriate promoter conferring gene expression in a timely, cell or tissue specific manner Preferred are promoters driving constitutive expression (Benfey et al., 1989 EMBO J. 8:2195-2202) like those derived from plant viruses like the 358 CAMV (Franck et al., 1980 Cell 21:285-294), the 19S CaMV (see also U.S. Pat. No. 5,352,605 and PCT Application No. WO 8402913) or plant promoters like those from Rubisco small subunit described in U.S. Pat. No. 4,962,028.

Other preferred sequences for use in plant gene expression cassettes are targeting-sequences necessary to direct the gene product in its appropriate cell compartment (for review see Kermode, 1996 Crit. Rev. Plant Sci. 15(4):285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (for review see Gatz, 1997 Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992 Plant J. 2:397-404) and an ethanol inducible promoter (PCT Application No. WO 93/21334).

Also, suitable promoters responding to biotic or abiotic stress conditions are those such as the pathogen inducible PRP1-gene promoter (Ward et al., 1993 Plant. Mol. Biol. 22:361-366), the heat inducible hsp80-promoter from tomato (U.S. Pat. No. 5,187,267), cold inducible alpha-amylase promoter from potato (PCT Application No. WO 96/12814) or the wound-inducible pinII-promoter (European Patent No. 375091). For other examples of drought, cold, and salt-inducible promoters, such as the RD29A promoter, see Yamaguchi-Shinozalei et al. (1993 Mol. Gen. Genet. 236:331-340).

Especially preferred are those promoters that confer gene expression in specific tissues and organs, such as guard cells and the root hair cells. Suitable promoters include the napin-gene promoter from rapeseed (U.S. Pat. No. 5,608,152), the USP-promoter from *Vicia faba* (Baeumlein et al., 1991 Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504, 200), the Bce4-promoter from *Brassica* (PCT Application No. WO 91/13980) or the legumin B4 promoter (LeB4; Baeumlein et al., 1992 Plant Journal, 2(2):233-9) as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, maize zein gene, oat glutelin gene, *Sorghum* kasirin-gene and rye secalin gene).

Also especially suited are promoters that confer plastid-specific gene expression since plastids are the compartment where lipid biosynthesis occurs. Suitable promoters are the viral RNA-polymerase promoter described in PCT Application No. WO 95/16783 and PCT Application No. WO 97/06250 and the clpP-promoter from *Arabidopsis* described in PCT Application No. WO 99/46394.

The invention further provides a recombinant expression vector comprising a PHSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a PHSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus wherein antisense nucleic acids are produced under the control of a high efficiency regulatory region. The activity of the regulatory region can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986 and Mol et al., 1990 FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PHSRP can be expressed in bacterial cells such as C. glutamicum, insect cells, fungal cells or mammalian cells (such as Chinese hamster ovary cells (CHO) or COS cells), algae, ciliates, plant cells, fungi or other microorganisms like C. glutamicum. Other suitable host cells are known to those skilled in the art.

Vector DNA can be introduced into prokaryotic or eukaryotic cells via conventional transformation or transfection techniques. As used herein, the terms "transformation", "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer and electroporation. Suitable methods for transforming or transfecting host cells including plant cells can be found in Sambrook, et al., (Molecular Cloning: A Laboratory Manual. $2^{nd}$, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, Agrobacterium protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses and forage crops, these crop plants are also preferred target plants for a genetic engineering as one further embodiment of the present invention.

In particular, the invention provides a method of producing a transgenic plant with a PHSRP coding nucleic acid, wherein expression of the nucleic acid(s) in the plant results in increased tolerance to environmental stress as compared to a wild type variety of the plant comprising: (a) transforming a plant cell with an expression vector comprising a PHSRP nucleic acid, and (b) generating from the plant cell a transgenic plant with a increased tolerance to environmental stress as compared to a wild type variety of the plant. The invention also provides a method of increasing expression of a gene of interest within a host cell as compared to a wild type variety of the host cell, wherein the gene of interest is transcribed in response to a PHSRP, comprising: (a) transforming the host cell with an expression vector comprising a PHSRP coding nucleic acid, and (b) expressing the PHSRP within the host cell, thereby increasing the expression of the gene transcribed in response to the PHSRP, as compared to a wild type variety of the host cell.

For such plant transformation, binary vectors such as pBinAR can be used (Höfgen and Willmitzer, 1990 Plant Science 66:221-230). Construction of the binary vectors can be performed by ligation of the cDNA in sense or antisense orientation into the T-DNA. Five-prime to the cDNA, a plant promoter activates transcription of the cDNA. A polyadenylation sequence is located 3-prime to the cDNA. Tissue-specific expression can be achieved by using a tissue specific promoter. For example, seed-specific expression can be achieved by cloning the napin or LeB4 or USP promoter 5-prime to the cDNA. Also, any other seed specific promoter element can be used. For constitutive expression within the whole plant, the CaMV 35S promoter can be used. The expressed protein can be targeted to a cellular compartment using a signal peptide, for example for plastids, mitochondria or endoplasmic reticulum (Kermode, 1996 Crit. Rev. Plant Sci. 4 (15):285-423). The signal peptide is cloned 5-prime in frame to the cDNA to achieve subcellular localization of the fusion protein. Additionally, promoters that are responsive to abiotic stresses can be used with, such as the Arabidopsis promoter RD29A, the nucleic acid sequences disclosed herein. One skilled in the art will recognize that the promoter used should be operatively linked to the nucleic acid such that the promoter causes transcription of the nucleic acid which results in the synthesis of an mRNA which encodes a polypeptide. Alternatively, the RNA can be an antisense RNA for use in affecting subsequent expression of the same or another gene or genes.

Alternate methods of transfection include the direct transfer of DNA into developing flowers via electroporation or Agrobacterium mediated gene transfer. Agrobacterium mediated plant transformation can be performed using for example the GV3101 (pMP90) Koncz and Schell, 1986 Mol. Gen. Genet. 204:383-396) or LBA4404 (Clontech) Agrobacterium tumefaciens strain. Transformation can be performed by standard transformation and regeneration techniques (Deblaere et al., 1994 Nucl. Acids. Res. 13:4777-4788; Gelvin, Stanton B. and Schilperoort, Robert A, Plant Molecular Biology Manual, $2^{nd}$ Ed. —Dordrecht: Kluwer Academic Publ., 1995. —in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993. —360 S., ISBN 0-8493-5164-2). For example, rapeseed can be transformed via cotyledon or hypocotyl transformation (Moloney et al., 1989 Plant Cell Report 8:238-242; De Block et al., 1989 Plant Physiol. 91:694-701). Use of antibiotics for Agrobacterium and plant selection depends on the binary vector and the Agrobacterium strain used for transformation. Rapeseed selection is normally performed using kanamycin as selectable plant marker. Agrobacterium mediated gene transfer to flax can be performed using, for example, a technique described by Mlynarova et al., 1994 Plant Cell Report 13:282-285. Additionally, transformation of soybean can be performed using, for example, a technique described in European Patent No. 0424 047, U.S. Pat. No. 5,322,783, European Patent Application No. 0397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique. (See, for example, Freeling and Walbot "The Maize Handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate or in plants that confer resistance towards a herbicide such as glyphosate or glufosinate. Nucleic acid molecules encoding a selectable marker can be introduced into a host cell on the same vector as that encoding a PHSRP or can be introduced on a separate vector. Cells stably transfected with the introduced nucleic acid molecule can be identified by, for example, drug selection (e.g., cells that have incorporated the selectable marker gene will survive, while the other cells die).

To create a homologous recombinant microorganism, a vector is prepared which contains at least a portion of a PHSRP gene into which a deletion, addition or substitution has been introduced to thereby alter, e.g., functionally disrupt, the PHSRP gene. Preferably, the PHSRP gene is a *Physcomitrella patens* PHSRP gene, but it can be a homolog from a related plant or even from a mammalian, yeast, or insect source. In a preferred embodiment, the vector is designed such that, upon homologous recombination, the endogenous PHSRP gene is functionally disrupted (i.e., no longer encodes a functional protein; also referred to as a knock-out vector). Alternatively, the vector can be designed such that, upon homologous recombination, the endogenous PHSRP gene is mutated or otherwise altered but still encodes a functional protein (e.g., the upstream regulatory region can be altered to thereby alter the expression of the endogenous PHSRP). To create a point mutation via homologous recombination, DNA-RNA hybrids can be used in a technique known as chimeraplasty (Cole-Strauss et al., 1999 Nucleic Acids Research 27(5):1323-1330 and Kmiec, 1999 Gene therapy American Scientist. 87(3):240-247). Homologous recombination procedures in *Physcomitrella patens* are also well known in the art and are contemplated for use herein.

Whereas in the homologous recombination vector, the altered portion of the PHSRP gene is flanked at its 5' and 3' ends by an additional nucleic acid molecule of the PHSRP gene to allow for homologous recombination to occur between the exogenous PHSRP gene carried by the vector and an endogenous PHSRP gene, in a microorganism or plant. The additional flanking PHSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95 (8):4368-4373 for cDNA based recombination in *Physcomitrella patens*). The vector is introduced into a microorganism or plant cell (e.g., via polyethylene glycol mediated DNA), and cells in which the introduced PHSRP gene has homologously recombined with the endogenous PHSRP gene are selected using art-known techniques.

In another embodiment, recombinant microorganisms can be produced that contain selected systems which allow for regulated expression of the introduced gene. For example, inclusion of a PHSRP gene on a vector placing it under control of the lac operon permits expression of the PHSRP gene only in the presence of IPTG. Such regulatory systems are well known in the art.

A host cell of the invention, such as a prokaryotic or eukaryotic host cell in culture, can be used to produce (i.e., express) a PHSRP. Accordingly, the invention further provides methods for producing PHSRPs using the host cells of the invention. In one embodiment, the method comprises culturing the host cell of invention (into which a recombinant expression vector encoding a PHSRP has been introduced, or into which genome has been introduced a gene encoding a wild-type or altered PHSRP) in a suitable medium until PHSRP is produced. In another embodiment, the method further comprises isolating PHSRPs from the medium or the host cell.

Another aspect of the invention pertains to isolated PHSRPs, and biologically active portions thereof. An "isolated" or "purified" protein or biologically active portion thereof is free of some of the cellular material when produced by recombinant DNA techniques, or chemical precursors or other chemicals when chemically synthesized. The language "substantially free of cellular material" includes preparations of PHSRP in which the protein is separated from some of the cellular components of the cells in which it is naturally or recombinantly produced. In one embodiment, the language "substantially free of cellular material" includes preparations of a PHSRP having less than about 30% (by dry weight) of non-PHSRP material (also referred to herein as a "contaminating protein"), more preferably less than about 20% of non-PHSRP material, still more preferably less than about 10% of non-PHSRP material, and most preferably less than about 5% non-PHSRP material.

When the PHSRP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of PHSRP in which the protein is separated from chemical precursors or other chemicals that are involved in the synthesis of the protein. In one embodiment, the language "substantially free of chemical precursors or other chemicals" includes preparations of a PHSRP having less than about 30% (by dry weight) of chemical precursors or non-PHSRP chemicals, more preferably less than about 20% chemical precursors or non-PHSRP chemicals, still more preferably less than about 10% chemical precursors or non-PHSRP chemicals, and most preferably less than about 5% chemical precursors or non-PHSRP chemicals. In preferred embodiments, isolated proteins, or biologically active portions thereof, lack contaminating proteins from the same organism from which the PHSRP is derived. Typically, such proteins are produced by recombinant expression of, for example, a *Physcomitrella patens* PHSRP in plants other than *Physcomitrella patens* or microorganisms such as *C. glutamicum*, ciliates, algae or fungi.

The nucleic acid molecules, proteins, protein homologs, fusion proteins, primers, vectors, and host cells described herein can be used in one or more of the following methods: identification of *Physcomitrella patens* and related organisms; mapping of genomes of organisms related to *Physcomitrella patens*; identification and localization of *Physcomi-*

*trella patens* sequences of interest; evolutionary studies; determination of PHSRP regions required for function; modulation of a PHSRP activity; modulation of the metabolism of one or more cell functions; modulation of the transmembrane transport of one or more compounds; and modulation of stress resistance.

The moss *Physcomitrella patens* represents one member of the mosses. It is related to other mosses such as *Ceratodon purpureus* which is capable of growth in the absence of light. Mosses like *Ceratodon* and *Physcomitrella* share a high degree of homology on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The PHSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a PHSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass and forage crops, for example.

In particular, the present invention describes using the expression of PP2A-2 (SEQ ID NO:11), PP2A-3 (SEQ ID NO:12), PP2A-4 (SEQ ID NO:13), PP2C-1 (SEQ ID NO:14) and PP2C-2 (SEQ ID NO:15) of *Physcomitrella patens* to engineer drought-tolerant, salt-tolerant or cold-tolerant plants. This strategy has herein been demonstrated for *Arabidopsis thaliana*, Rapeseed/Canola, soybeans, corn and wheat but its application is not restricted to these plants. Accordingly, the invention provides a transgenic plant containing a PHSRP selected from a protein phosphatase 2A or a protein phosphatase 2C, wherein the environmental stress is drought, increased salt or decreased temperature. In preferred embodiments, the environmental stress is drought or decreased temperature.

The present invention also provides methods of modifying stress tolerance of a plant comprising, modifying the expression of a PHSRP in the plant. The invention provides that this method can be performed such that the stress tolerance is either increased or decreased. In particular, the present invention provides methods of producing a transgenic plant having an increased tolerance to environmental stress as compared to a wild type variety of the plant comprising increasing expression of a PHSRP in a plant.

The methods of increasing expression of PHSRPs can be used wherein the plant is either transgenic or not transgenic. In cases when the plant is transgenic, the plant can be transformed with a vector containing any of the above described PHSRP coding nucleic acids, or the plant can be transformed with a promoter that directs expression of native PHSRP in the plant, for example. The invention provides that such a promoter can be tissue specific. Furthermore, such a promoter can be developmentally regulated. Alternatively, non-transgenic plants can have native PHSRP expression modified by inducing a native promoter.

The expression of PP2A-2 (SEQ ID NO:1), PP2A-3 (SEQ ID NO:12), PP2A-4 (SEQ ID NO:13), PP2C-1 (SEQ ID NO:14) and PP2C-2 (SEQ ID NO:15) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657). The later case involves identification of the PP2A-2 (SEQ ID NO:11), PP2A-3 (SEQ ID NO:12), PP2A-4 (SEQ ID NO:13), PP2C-1 (SEQ ID NO:14) and PP2C-2 (SEQ ID NO:15) homologs in the target plant as well as from its promoter. Zinc-finger-containing recombinant transcription factors are engineered to specifically interact with the PP2A-2 (SEQ ID NO:11), PP2A-3 (SEQ ID NO:12), PP2A-4 (SEQ 10 NO:13), PP2C-1 (SEQ ID NO:14) and PP2C-2 (SEQ ID NO:15) homolog and transcription of the corresponding gene is activated.

In addition to introducing the PHSRP nucleic acid sequences into transgenic plants, these sequences can also be used to identify an organism as being *Physcomitrella patens* or a close relative thereof. Also, they may be used to identify the presence of *Physcomitrella patens* or a relative thereof in a mixed population of microorganisms. The invention provides the nucleic acid sequences of a number of *Physcomitrella patens* genes; by probing the extracted genomic DNA of a culture of a unique or mixed population of microorganisms under stringent conditions with a probe spanning a region of a *Physcomitrella patens* gene which is unique to this organism, one can ascertain whether this organism is present.

Further, the nucleic acid and protein molecules of the invention may serve as markers for specific regions of the genome. This has utility not only in the mapping of the genome, but also in functional studies of *Physcomitrella patens* proteins. For example, to identify the region of the genome to which a particular *Physcomitrella patens* DNA-binding protein binds, the *Physcomitrella patens* genome could be digested, and the fragments incubated with the DNA-binding protein. Those fragments that bind the protein may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related mosses.

The PHSRP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein that are essential for the functioning of the enzyme. This type of determination is of value for protein engineering studies and may give an indication of what the protein can tolerate in terms of mutagenesis without losing function.

Manipulation of the PHSRP nucleic acid molecules of the invention may result in the production of PHSRPs having functional differences from the wild-type PHSRPs. These proteins may be improved in efficiency or activity, may be present in greater numbers in the cell than is usual, or may be decreased in efficiency or activity.

There are a number of mechanisms by which the alteration of a PHSRP of the invention may directly affect stress response and/or stress tolerance. In the case of plants expressing PHSRPs, increased transport can lead to improved salt and/or solute partitioning within the plant tissue and organs. By either increasing the number or the activity of transporter molecules which export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim; Belter, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their tolerance to drought, salt, and temperature stress.

The engineering of one or more PHSRP genes of the invention may also result in PHSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226-235). While these products are typically excreted, cells can be genetically altered to transport more products than is typical for a wild-type cell. By optimizing the activity of one or more PHSRPs of the invention which are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998 The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation see U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246-252.

The aforementioned mutagenesis strategies for PHSRPs resulting in increased stress resistance are not meant to be limiting; variations on these strategies will be readily apparent to one skilled in the art. Using such strategies, and incorporating the mechanisms disclosed herein, the nucleic acid and protein molecules of the invention may be utilized to generate algae, ciliates, plants, fungi or other microorganisms like *C. glutamicum* expressing mutated PHSRP nucleic acid and protein molecules such that the stress tolerance is improved.

The present invention also provides antibodies that specifically bind to a PHSRP, or a portion thereof, as encoded by a nucleic acid described herein. Antibodies can be made by many well-known methods (See, e.g. Harlow and Lane, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163-167; Bebbington et al., 1992 Bio/Technology 10:169-175).

The phrases "selectively binds" and "specifically binds" with the polypeptide refer to a binding reaction that is determinative of the presence of the protein in a heterogeneous population of proteins and other biologics. Thus, under designated immunoassay conditions, the specified antibodies bound to a particular protein do not bind in a significant amount to other proteins present in the sample. Selective binding of an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *Physcomitrella patens* (Hedw.) B.S.G. from the collection of the genetic studies section of the University of Hamburg were used. They originate from the strain 16/14 collected by H. L. K. Whitehouse in Gransden Wood, Huntingdonshire England), which was subcultured from a spore by Engel (1968, Am. J. Bot. 55, 438-446). Proliferation of the plants was carried out by means of spores and by means of regeneration of the gametophytes. The protonema developed from the haploid spore as a chloroplast-rich chloronema and chloroplast-low cautionema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol s$^{-1}$ m$^{-2}$ (white light; Philips TL 65W/25 fluorescent tube) and a light/dark change of 16/8 hours. The moss was either modified in liquid culture using Knop medium according to Reski and Abel (1985, Planta 165:354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-lautylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 μl of N-laurylsarcosine buffer, 20 μl of β-mercaptoethanol and 10 μl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 μl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken tip in 50 μl of H$_2$O+RNAse (50 mg/ml final concentration). The DNA was dissolved overnight at 4° C. and the RNAse digestion was subsequently carried out at 37° C. for 1 hour Storage of the DNA took place at 4° C.

Example 3

Isolation of Total RNA and Poly-(A)+RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al. 1994, Mol. Gen. Genet., 244:352-359). The Poly(A)+ RNA was isolated using Dyna Beads$^R$ (Dynal, Oslo, Norway) following the instructions of the manufacturers protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany), Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands. Plasmid DNA was prepared from overnight grown *E. coli* cultures grown in Luria-Broth medium containing ampicillin (see Sambrook et al. 1989 Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'      SEQ ID NO: 16

5'-CTAAAGGGAACAAAAGCTG-3'     SEQ ID NO: 17

5'-TGTAAAACGACGGCCAGT-3'      SEQ ID NO: 18
```

Sequences were processed and annotated using the software package EST-MAX commercially provided by Bio-Max (Munich, Germany). The program incorporates practically all bioinformatics methods important for functional and structural characterization of protein sequences. For reference the website at pedant.mips.biochem.mpg.de. The most important algorithms incorporated in EST-MAX are: FASTA: Very sensitive sequence database searches with estimates of statistical significance; Pearson W. R. (1990) Rapid and sensitive sequence comparison with FASTP and FASTA. Methods Enzymol. 183:63-98; BLAST: Very sensitive sequence database searches with estimates of statistical significance. Altschul S. F., Gish W., Miller W., Myers E. W., and Lipman D. J. Basic local alignment search tool. Journal of Molecular Biology 215:403-10; PREDATOR: High-accuracy secondary structure prediction from single and multiple sequences. Frishman, D. and Argos, P. (1997) 75% accuracy in protein secondary structure prediction. Proteins, 27:329-335; CLUSTALW: Multiple sequence alignment. Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680; TMAP: Transmembrane region prediction from multiply aligned sequences. Persson, B. and Argos, P. (1994) Prediction of transmembrane segments in proteins utilizing multiple sequence alignments. J. Mol. Biol. 237:182-192; ALOM2: Transmembrane region prediction from single sequences. Klein, P., Kanehisa, M., and DeLisi, C. Prediction of protein function from sequence properties: A discriminate analysis of a database. Biochim. Biophys. Acta 787:221-226 (1984). Version 2 by Dr. K. Nakai; PROSEARCH: Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919-921; BLIMPS: Similarity searches against a database of ungapped blocks. J. C. Wallace and Henikoff S., (1992); PATMAT: A searching and extraction program for sequence, pattern and block queries and databases, CABIOS 8:249-254. Written by Bill Alford.

Example 5

Identification of *Physcomitrella patens* ORFs Corresponding to PP2A-2, PP2A-3, PP2A-4, PP2C-1 and PP2C-2

The *Physcomitrella patens* partial cDNAs (ESTs) shown in Table 1 below were identified in the *Physcomitrella patens* EST sequencing program using the program EST-MAX through BLAST analysis. The Sequence Identification Numbers corresponding to these ESTs are as follows: PP2A-2 (SEQ ID NO:1), PP2A-3 (SEQ ID NO:2), PP2A-4 (SEQ ID NO:3), PP2C-1 (SEQ ID NO:4) and PP2C-2 (SEQ ID NO:5). PP2A-2 and PP2A-3 are homologous to the regulatory subunit of protein phosphatase 2A from human and plants, respectively. On the other hand, PP2A-4 has homology with the catalytic subunit of several plant protein phosphatase 2A. The predicted proteins of PP2C-1 and PP2C-2 are homologous to several eukaryotic protein phosphatase 2Cs.

TABLE 1

| Name | Functional Category | Function | Sequence Code | ORF position |
| --- | --- | --- | --- | --- |
| PP2A-2 | Protein phosphatase | protein phosphatase 2A 62 kDa B | c_pp004055020r | 77-466 |
| PP2A-3 | Protein phosphatase | type 2A protein serine/threonine phosphatase 55 kD | c_pp004077320r | 86-550 |
| PP2A-4 | Protein phosphatase | serine/threonine phosphatase | s_pp001008094f | 1-440 |
| PP2C-1 | Protein phosphatase | protein phosphatase 2C-like protein | c_pp004071042r | 63-590 |
| PP2C-2 | Protein phosphatase | protein phosphatase-2c | s_pp004077230r | 264-554 |

TABLE 2

Degree of amino acid identity and similarity of PpPP2A-2 and other homologous proteins (GCG Gap program was used: gap penalty: 10; gap extension penalty: 0.1; score matrix: blosum62)

| | Swiss-Prot # | | | | |
|---|---|---|---|---|---|
| | Q9XGR4 | Q06190 | Q9Z176 | Q9Y5P8 | Q9NKH5 |
| Protein name | PROTEIN PHOSPHATASE 2A 62 KDA B" REGULATORY SUBUNIT | SERINE/THREONINE PROTEIN PHOSPHATASE 2A, 72/130 KDA REGULATORY SUBUNIT B | PROTEIN PHOSPHATASE 2A, 59 KDA REGULATORY SUBUNIT B | SERINE/THREONINE PROTEIN PHOSPHATASE 2A, 48 KDA REGULATORY SUBUNIT B | PROTEIN PHOSPHATASE 2A RELATED PROTEIN |
| Species | *Arabidopsis thaliana* (Mouse-ear cress) | *Homo sapiens* (Human) | *Mus musculus* (Mouse) | *Homo sapiens* (Human) | *Leishmania major* |
| Identity % | 60% | 33% | 37% | 39% | 31% |
| Similarity % | 70% | 48% | 51% | 55% | 44% |

TABLE 3

Degree of amino acid identity and similarity of PpPP2A-3 and other homologous proteins (GCG Gap program was used: gap penalty: 10; gap extension penalty: 0.1; score matrix: blosum62)

| | Swiss-Prot # | | | | |
|---|---|---|---|---|---|
| | Q39247 | O82774 | Q38821 | Q9Y0A6 | O94180 |
| Protein name | TYPE 2A PROTEIN SERINE/THREONINE PHOSPHATASE 55 KDA B REGULATORY SUBUNIT | PROTEIN PHOSPHATASE 2A 55 KDA B REGULATORY SUBUNIT | 55 KDA B REGULATORY SUBUNIT OF PHOSPHATASE 2A | PROTEIN PHOSPHATASE 2A B55 REGULATORY SUBUNIT | PROTEIN PHOSPHATASE 2A REGULATORY B SUBUNIT |
| Species | *Arabidopsis thaliana* (Mouse-ear cress) | *Oryza sativa* (Rice) | *Arabidopsis thaliana* (Mouse-ear cress) | *Dictyostelium discoideum* (Slime mold) | *Neurospora crassa* |
| Identity % | 67% | 64% | 64% | 48% | 47% |
| Similarity % | 75% | 73% | 73% | 59% | 58% |

TABLE 4

Degree of amino acid identity and similarity of PpPP2A-4 and other homologous proteins (GCG Gap program was used: gap penalty: 10; gap extension penalty: 0.1; score matrix: blosum62)

| | Swiss-Prot # | | | | |
|---|---|---|---|---|---|
| | Q9MB06 | Q07098 | Q9MB05 | Q9ZSE4 | Q07099 |
| Protein name | TYPE 2A PROTEIN PHOSPHATASE-1 | SERINE/THREONINE PROTEIN PHOSPHATASE PP2A-1 CATALYTIC SUBUNIT | TYPE 2A PROTEIN PHOSPHATASE-2 | SERINE/THREONINE PROTEIN PHOSPHATASE PP2A CATALYTIC SUBUNIT | SERINE/THREONINE PROTEIN PHOSPHATASE PP2A-2 CATALYTIC SUBUNIT |
| Species | *Vicia faba* (Broad bean) | *Arabidopsis thaliana* (Mouse-ear cress) | *Vicia faba* (Broad bean) | *Hevea brasiliensis* (Para rubber tree) | *Arabidopsis thaliana* (Mouse-ear cress) |
| Identity % | 91% | 90% | 90% | 89% | 90% |
| Similarity % | 94% | 94% | 93% | 93% | 94% |

TABLE 5

Degree of amino acid identity and similarity of PpPP2C-1 and other homologous proteins (GCG Gap program was used: gap penalty: 10; gap extension penalty: 0.1; score matrix: blosum62)

| | Swiss-Prot # | | | | |
|---|---|---|---|---|---|
| | O81716 | Q9SZ53 | Q09172 | P49444 | P49596 |
| Protein name | PROTEIN PHOSPHATASE 2C | PROTEIN PHOSPHATASE 2C-LIKE PROTEIN | PROTEIN PHOSPHATASE 2C HOMOLOG 2 | PROTEIN PHOSPHATASE 2C | PROBABLE PROTEIN PHOSPHATASE 2C T23F11.1 |
| Species | Arabidopsis thaliana (Mouse-ear cress) | Arabidopsis thaliana (Mouse-ear cress) | Schizosaccharomyces pombe (Fission yeast) | Paramecium tetraurelia | Caenorhabditis elegans |
| Identity % | 51% | 52% | 33% | 36% | 32% |
| Similarity % | 64% | 64% | 42% | 49% | 43% |

TABLE 6

Degree of amino acid identity and similarity of PpPP2C-2 and other homologous proteins (GCG Gap program was used: gap penalty: 10; gap extension penalty: 0.1; score matrix: blosum62)

| | Swiss-Prot # | | | | |
|---|---|---|---|---|---|
| | Q9ZSQ7 | Q9M3V0 | Q9LHJ9 | Q9M2W1 | Q9LSN8 |
| Protein name | PROTEIN PHOSPHATASE 2C HOMOLOG | PROTEIN PHOSPHATASE 2C (PP2C) | PROTEIN PHOSPHATASE 2C | PROTEIN PHOSPHATASE 2C-LIKE PROTEIN | PROTEIN PHOSPHATASE 2C-LIKE PROTEIN |
| Species | Mesembryanthemum crystallinum (Common ice plant) | Fagus sylvatica (Beechnut) | Arabidopsis thaliana (Mouse-ear cress) | Arabidopsis thaliana (Mouse-ear cress) | Arabidopsis thaliana (Mouse-ear cress) |
| Identity % | 57% | 57% | 56% | 49% | 52% |
| Similarity % | 70% | 69% | 69% | 62% | 67% |

Example 6

Cloning of the Full-Length *Physcomitrella patens* cDNA Encoding for PP2A-2, PP2A-3, PP2A-4, PP2C-1 and PP2C-2

To isolate full-length PP2A-2 (SEQ ID NO:6), PP2A-3 (SEQ ID NO:7), PP2A-4 (SEQ ID NO:8) and PP2C-2 (SEQ ID NO:10) from *Physcomitrella patens*, cDNA libraries were created with SMART RACE cDNA Amplification kit (Clontech Laboratories) following manufacturer's instructions. Total RNA isolated as described in Example 2 was used as the template. The cultures were treated prior to RNA isolation as follows: Salt Stress: 2, 6, 12, 24, 48 hours with 1-M NaCl-supplemented medium; Cold Stress: 4° C. for the same time points as for salt; Drought Stress: cultures were incubated on dry filter paper for the same time points as for salt.

5' RACE Protocol

The EST sequences PP2A-2 (SEQ ID NO:1), PP2A-3 (SEQ ID NO:2), PP2A-4 (SEQ ID NO:3) and PP2C-2 (SEQ ID NO:5) identified from the database search as described in Example 4 were used to design oligos for RACE (see Table 5). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions. The sequences obtained from the RACE reactions corresponded to full-length coding regions of PP2A-2, PP2A-3, PP2A-4 and PP2C-2 and were used to design oligos for full-length cloning of the respective genes (see below full-length amplification).

Full-Length Amplification

Full-length clones corresponding PP2A-2 (SEQ ID NO:1), PP2A-3 (SEQ ID NO:2), PP2A-4 (SEQ ID NO:3), PP2C-1 (SEQ ID NO:4) and PP2C-2 (SEQ ID NO:5) were obtained by performing polymerase chain reaction (PCR) with gene-specific primers (see Table 7) and the original EST as the template. The conditions for the reaction were standard conditions with PWO DNA polymerase (Roche). PCR was performed according to standard conditions and to manufacturer's protocols (Sambrook et al., 1989 Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C. followed by five cycles of one minute at 94° C., one minute at 50° C. and 1.5 minutes at 72° C. This was followed by twenty five cycles of one minute at 94° C., one minute at 65° C. and 1.5 minutes at 72° C.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al. 1989, Molecular Cloning, A Laboratory Manual. 2nd Edition. Cold Spring Harbor Laboratory Press. Cold Spring Harbor, N.Y.). Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989 Molecular Cloning, A Laboratory Manual. 2nd Edition. Cold Spring Harbor Laboratory Press. Cold Spring Harbor, N.Y.).

TABLE 7

Scheme and primers used for cloning of full-length clones

| Gene | Sites in the final product | Isolation Method | Primers Race | Primer RT-PCR |
|---|---|---|---|---|
| PpPP2A-2 | XmaI/HpaI | 5' RACE and RT-PCR for Full-length clone | RC215: (SEQ ID NO: 19) CTGCCGTTGGA GGCATCCTCGC CATC | RC699: (SEQ ID NO: 20) ATCCCGGGCATCG GGAAGACGGTGTG TGTGTGTG RC700: (SEQ ID NO: 21) GCGTTAACGCTAC CAGCCTCGGGCTG AACCAGTC |
| PpPP2A-3 | XmaI/HpaI | 5' RACE and RT-PCR for Full-length clone | RC214: (SEQ ID NO: 22) GGAGCCCTTGC TGCTACTGTAT GCT | RC594: (SEQ ID NO: 23) ATCCCGGGTGGTG GTGGCGGTGAAGT TATTAC RC595: (SEQ ID NO: 24) GCGTTAACATGTA CAACCTGTTGGAT GCAGC |
| PpPP2A-4 | HpaI/SacI | 5' RACE and RT-PCR for Full-length clone | RC213: (SEQ ID NO: 25) ACATCGCGCCC TCGTGCGGCAC TTC | RC658: (SEQ ID NO: 26) GCGTTAACGCGCG GAGGAGAGCGGAT CGGTTAG RC659: (SEQ ID NO: 27) GCGAGCTCGAGCA TGCCATATACAGT AGGTGTG |
| PpPP2C-1 | EcoRV/Eco RV | RT-PCR for Full-length clone | | RC413: (SEQ ID NO: 28) GCGATATCGATTT GCAAGGGCGAAGT GCACAAGA RC414: (SEQ ID NO: 29) GCGATATCGAAGG CAGAAGGCAACTC CCAGTT |
| PpPP2C-2 | XmaI/SacI | 5' RACE and RT-PCR for Full-length clone | RC207: (SEQ ID NO: 30) CACTCCCACAC CACACCTACCA GGCA RC682: (SEQ ID NO: 31) GGGCTTCGTGA GCCATGAATCC CTT | RC862: (SEQ ID NO: 32) ATCCCGGGCGTGG AAGGAGAGGCGAA TGTGGAGG RC863: (SEQ ID NO: 33) GCGAGCTCCTGTG GGTGTCTAGCTTC AGGTTC |

Example 7

Engineering Stress-Tolerant *Arabidopsis* Plants by Over-Expressing the Genes PP2A-2, PP2A-3, PP2A-4, PP2C-1 and PP2C-2

Binary Vector Construction: Kanamycin

The pACGH101 (BPS-Cyanmid) vector was digested with PstI (Roche) and FseI (NEB) according to manufacturers' instructions. The fragment was purified by agarose gel and extracted via the Qiaex II DNA Extraction kit (Qiagen). This resulted in a vector fragment with the *Arabidopsis* Actin2 promoter with internal intron and the OCS3 terminator. Primers for PCR amplification of the NPTII gene were designed as follows:

```
5'NPT-Pst:
                                        (SEQ ID NO: 34)
GCG-CTG-CAG-ATT-TCA-TTT-GGA-GAG-GAC-ACG

3'NPT-Fse:
                                        (SEQ ID NO: 35)
CGC-GGC-CGG-CCT-CAG-AAG-AAC-TCG-TCA-AGA-AGG-CG
```

The 0.9 kilobase NPTII gene was amplified via PCR from pCambia 2301 plasmid DNA [94° C. 60 sec, {94° C. 60 sec, 61° C. (−0.1° C. per cycle) 60 sec, 72° C. 2 min}×25 cycles, 72° C. 10 min on Biometra T-Gradient machine], and purified via the Qiaquick PCR Extraction kit (Qiagen) as per manufacturer's instructions. The PCR DNA was then subcloned into the pCR-BluntII TOPO vector (Invitrogen) pursuant to the manufacturer's instructions (NPT-Topo construct). These ligations were transformed into Top10 cells (Invitrogen) and grown on LB plates with 50 µg/ml kanamycin sulfate overnight at 37° C. Colonies were then used to inoculate 2 ml LB media with 50 µg/ml kanamycin sulfate and grown overnight at 37° C. Plasmid DNA was recovered using the Qiaprep Spin Miniprep kit (Qiagen) and sequenced in both the 5' and 3' directions using standard conditions. Subsequent analysis of the sequence data using VectorNTI software revealed no PCR errors present in the NPTII gene sequence.

The NPT-Topo construct was then digested with PstI (Roche) and FseI (NEB) according to manufacturers' instructions. The 0.9 kilobase fragment was purified on agarose gel and extracted by Qiaex II DNA Extraction kit (Qiagen). The Pst/Fse insert fragment from NPT-Topo and the Pst/Fse vector fragment from pACGH101 were then ligated together using T4 DNA Ligase (Roche) following manufacturer's instructions. The ligation was then transformed into Top10 cells (Invitrogen) under standard conditions, creating pBPSsc019 construct. Colonies were selected on LB plates with 50 ug/ml kanamycin sulfate and grown overnight at 37° C. These colonies were then used to inoculate 2 ml LB media with 50 µg/ml kanamycin sulfate and grown overnight at 37° C. Plasmid DNA was recovered using the Qiaprep Spin Miniprep kit (Qiagen) following the manufacturer's instructions.

The pBPSSC019 construct was digested with KpnI and BsaI (Roche) according to manufacturer's instructions. The fragment was purified via agarose gel and then extracted via the Qiaex II DNA Extraction kit (Qiagen) as per its instructions, resulting in a 3 kilobase Act-NPT cassette, which included the *Arabidopsis* Actin2 promoter with internal intron, the NPTII gene and the OCS3 terminator.

The pBPSJH001 vector was digested with SpeI and ApaI (Roche) and blunt-end filled with Klenow enzyme and 0.1 mM dNTPs (Roche) according to manufacture's instructions. This produced a 10.1 kilobase vector fragment minus the Gentamycin cassette, which was recircularized by self-ligating with T4 DNA Ligase (Roche), and transformed into Top10 cells (Invitrogen) via standard conditions. Transformed cells were selected for on LB agar containing 50 µg/ml kanmycin sulfate and grown overnight at 37° C. Colonies were then used to inoculate 2 ml of liquid LB containing 50 µg/ml kanamycin sulfate and grown overnight at 37° C. Plasmid DNA was extracted using the QIAprep Spin Miniprep Kit (Qiagen) following manufacture's instructions. The recirularized plasmid was then digested with KpnI (Roche) and extracted from agarose gel via the Qiaex II DNA Extraction kit (Qiagen) as per manufacturers' instructions.

The Act-NPT Kpn-cut insert and the Kpn-cut pBPSJH001 recircularized vector were then ligated together using T4 DNA Ligase (Roche) and transformed into Top 10 cells (Invitrogen) as per manufacturers' instructions. The resulting construct, pBPSsc022, now contained the Super Promoter, the GUS gene, the NOS terminator, and the Act-NPT cassette. Transformed cells were selected for on LB agar containing 50 µg/ml kanamycin sulfate and grown overnight at 37° C. Colonies were then used to inoculate 2 ml of liquid LB containing 50 µg/ml kanamycin sulfate and grown overnight at 37° C. Plasmid DNA was extracted using the QIAprep Spin Miniprep Kit (Qiagen) following manufacturer's instructions. After confirmation of ligation success via restriction digests, pBPSsc022 plasmid DNA was further propagated and recovered using the Plasmid Midiprep Kit (Qiagen) following the manufacturer's instructions.

Subcloning of PP2A-2, PP2A-3, PP2A-4, PP2C-1 and PP2C-2 into the Binary Vector

The fragments containing the *Physcomitrella patens* different protein phosphatases were excised from the recombinant PCR2.1 TOPO vectors by double digestion with restriction enzymes (see Table 8) according to manufacturer's instructions. The subsequence fragment was excised from agarose gel with a QIAquick Gel Extraction Kit (QIAgen) according to manufacturer's instructions and ligated into the binary vector pBPSsc022, cleaved with appropriate enzymes (see Table 8) and dephosphorylated prior to ligation. The resulting recombinant pBPSsc022 vector contained the corresponding Phosphatase in the sense orientation under the control of the constitutive super promoter.

TABLE 8

Listed are the names of the various constructs of the *Physcomitrella patens* phosphatases used for plant transformation

| Gene | Enzymes used to generate gene fragment | Enzymes used to restrict pBPSJH001 | Binary Vector Construct |
|---|---|---|---|
| PpPP2A-2 | XmaI/HpaI | XmaI/Ecl136 | pBPSJYW023 |
| PpPP2A-3 | XmaI/HpaI | XmaI/Ecl136 | pBPSSY007 |
| PpPP2A-4 | HpaI/SacI | SmaI/SacI | pBPSJYW016 |
| PpPP2C-1 | EcoRV/EcoRV | SmaI/Ecl136 | pBPSJYW017 |
| PpPP2C-2 | XmaI/SacI | XmaI/SacI | PBPSERG014 |

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold 1993, Acad. Sci. Paris. 316:1194-1199; Bent et al. 1994, Science 265:1856-1860).

Screening of Transformed Plants

T1 seeds were sterilized according to standard protocols (Xiong et al. 1999, Plant Molecular Biology Reporter 17: 159-170). Seeds were plated on ½ Murashige and Skoog media (MS) (Sigma-Aldrich) pH 5.7 with KOH, 0.6% agar and supplemented with 1% sucrose, 0.5 g/L 2-[N-Morpholino]ethansulfonic acid (MES) (Sigma-Aldrich), 50 µg/ml kanamycin (Sigma-Aldrich), 500 µg/ml carbenicillan (Sigma-Aldrich) and 2 µg/ml benomyl (Sigma-Aldrich). Seeds on plates were vernalized for four days at 4° C. The seeds were germinated in a climatic chamber at an air temperature of 22° C. and light intensity of 40 micromols$^{-1m2}$ (white light; Philips TV 65W/25 fluorescent tube) and 16 hours light and 8 hours dark day length cycle. Transformed seedlings were selected after 14 days and transferred to ½ MS media pH 5.7 with KOH 0.6% agar plates supplemented with 0.6% agar, 1% sucrose, 0.5 g/L MES (Sigma-Aldrich), and 2 µg/ml benomyl (Sigma-Aldrich) and allowed to recover for five-seven days.

Drought Tolerance Screening

T1 seedlings were transferred to dry, sterile filter paper in a petri dish and allowed to desiccate for two hours at 80% RH (relative humidity) in a Percieval Growth Cabinet MLR-350H, micromols$^{-1m2}$ (white light; Philips TL 65W/25 fluorescent tube). The RH was then decreased to 60% and the seedlings were desiccated further for eight hours. Seedlings were then removed and placed on ½ MS 0.6% agar plates supplemented with 2 µg/ml benomyl (Sigma-Aldrich) and 0.54, MES (Sigma-Aldrich) and scored after five days.

Under drought stress conditions, PpPP2A-2 over-expressing Arabidopsis thaliana plants showed a 82% (9 survivors from 11 stressed plants) survival rate to the stress screening; PpPP2A-3, 50% (5 survivors from 10 stressed plants); PpPP2A-4, 58% (7 survivors from 12 stressed plants); PpPP2C-1, 100% (24 survivors from 24 stressed plants); and PpPP2C-2, 64% (7 survivors from 11 stressed plants), whereas the untransformed control only showed a 28% survival rate. It is noteworthy that the analyses of these transgenic lines were performed with T1 plants, and therefore, the results will be better when a homozygous, strong expresser is found.

TABLE 9

Summary of the drought stress tests

| | Drought Stress Test | | |
|---|---|---|---|
| Gene Name | Number of survivors | Total number of plants | Percentage of survivors |
| PpPP2A-2 | 9 | 11 | 82% |
| PpPP2A-3 | 5 | 10 | 50% |
| PpPP2A-4 | 7 | 12 | 58% |
| PpPP2C-1 | 24 | 24 | 100% |
| PpPP2C-2 | 7 | 11 | 64% |
| Control | 16 | 57 | 28% |

Freezing Tolerance Screening

Seedlings were moved to petri dishes containing ½ MS 0.6% agar supplemented with 2% sucrose and 2 µg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −10° C. decreasing −1° C. hour. The seedlings were then incubated at 5.0° C. for 24 hours and then allowed to thaw at 5° C. for 12 hours. The water was poured off and the seedlings were scored after 5 days.

Under freezing stress conditions, PpPP2A-2 over-expressing Arabidopsis thaliana plants showed a 58% (7 survivors from 12 stressed plants) survival rate; PpPP2A-4, 90% (9 survivors from 10 stressed plants), PpPP2C-1, 100% (21 survivors from 21 stressed plants) and PpPP2C-2, 57% (4 survivor from 7 stressed plants), whereas the untransformed control only showed a 2% (1 survivor from 48 tested plants) survival rate. It is noteworthy that the analyses of these transgenic lines were performed with T1 plants, and therefore, the results will be better when a homozygous, strong expresser is found.

TABLE 10

Summary of the freezing stress tests

| | Freezing Stress Test | | |
|---|---|---|---|
| Gene Name | Number of survivors | Total number of plants | Percentage of survivors |
| PpPP2A-2 | 7 | 12 | 58% |
| PpPP2A-4 | 9 | 10 | 90% |
| PpPP2C-1 | 21 | 21 | 100% |
| PpPP2C-2 | 4 | 7 | 57% |
| Control | 1 | 48 | 2% |

Salt Tolerance Screening

Seedlings were transferred to filter paper soaked in ½ MS and placed on ½ MS 0.6% agar supplemented with 2 µg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 µg/ml benomyl. The seedlings were scored after 5 days. The transgenic plants are then screened for their improved salt tolerance demonstrating that transgene expression confers salt tolerance.

Example 8

Detection of the PP2, 4-2, PP2A-3, PP2A-4, PP2C-1 and PP2C-2 Transgenes in the Transgenic Arabidopsis Lines To check for the presence of the PpPP2A-2, PpPP2A-3, PpPP2A-4, PpPP2C-1 and PpPP2C-2 transgene in transgenic Arabidopsis lines, PCR was performed on genomic DNA which contaminates the RNA samples taken as described in Example 9 below. 2.5 µl of RNA sample was used in a 50 µl PCR reaction using Taq DNA polymerase (Roche Molecular Biochemicals) according to the manufacturer's instructions. The primer for the binary vector region (5'GCTGACACGC-CAAGCCTCGCTAGTC3') (SEQ ID NO:36) and the gene specific 3' primer for each transgene which was used for the full-length RT-PCR (see Table 7) were used for the PCR. The PCR program was as following: 30 cycles of 1 minute at 94° C., 1 minute at 62° C. and 4 minutes at 70° C., followed by 10 minutes at 72° C. Binary vector plasmid with the transgenes cloned in was used as positive control, and the wild type C24 genomic DNA was used as negative control in the PCR reactions. 10 µl PCR reaction was analyzed on 0.8% agarose-ethidium bromide gel.

The transgenes with the expected size (for PpPP2A-2: 2.5 kb fragment; PpPP2A-3: 2.0 kb fragment; PpPP2A-4: 1.4 kb fragment; PpPP2C-1: 1.4 kb fragment; PpPP2C-2: 1.4 kb fragment) were successfully amplified from the T1 transgenic lines, but not from the wild-type C24. This result indicates that the T1 transgenic plants contain at least one copy of the transgenes. There was no indication of existence of either identical or very similar in untransformed *Arabidopsis thaliana* which can be amplified in this method in the wild-type plants.

Example 9

Detection of the PP2A-2Z PP2A-3, PP2A-4, PP2C-1 and PP2C-2 Transgene mRNA in Transgenic *Arabidopsis* Lines Transgene expression was detected using RT-PCR. Total RNA was isolated from stress-treated plants using a procedure adapted from (Verwoerd et al., 1989 NAR 17:2362). Leaf samples (50-100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH8, 10 mM EDTA, 1% SDS), followed by brief vortexing to mix. After the addition of 250 µl of chloroform, each sample was vortexed briefly. Samples were then centrifuged for 5 minutes at 12,000×g. The upper aqueous phase was removed to a fresh eppendorf tube. RNA was precipitated by adding $\frac{1}{10}^{th}$ volume 3M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 µl DEPC treated water.

To remove contaminating DNA from the samples, each was treated with RNase-free DNase (Roche) according to the manufacturer's recommendations. cDNA was synthesized from total RNA using the Superscript First-Strand Synthesis System for RT-PCR (Gibco-BRL) following manufacturer's recommendations. PCR amplification of a gene-specific fragment from the synthesized cDNA was performed using Taq DNA polymerase (Roche) and gene-specific primers as shown below in the following reaction: 1×PCR buffer, 1.5 mM $MgCl_2$, 0.2 µM each primer, 0.2 µM dNTPs, 1 unit polymerase, 5 µl cDNA from synthesis reaction. Amplification was performed under the following conditions: Predenaturation, 94° C., 3 minutes; denaturation, 94° C., 30 seconds; annealing, 62° C., 30 seconds; extension, 72° C., 2 minute, 30 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. These results indicated that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 7.

TABLE 11

Primers used for the amplification of respective transgene mRNA in PCR using RNA isolated from transgenic *Arabidopsis thaliana* plants as template

| Gene | 5' primer | 3' primer |
|---|---|---|
| PpPP2A-2 | 5'GCAGACGTATGGGAAC TAGCCACCT3' (SEQ ID NO: 37) | 5'CGCTCTACGATTCGGTA GGTGAGAGC3' (SEQ ID NO: 38) |
| PpPP2A-3 | 5'CTGGCGACAGAGGAGG ACGCGTTGT3' (SEQ ID NO: 39) | 5'GCGTAGGCTCTTCTACA TCTCGCAAC3' (SEQ ID NO: 40) |
| PpPP2A-4 | 5'CGGACGATCTTGGTGG AGGAGTGGAAC3' (SEQ ID NO: 41) | 5'GTGTCGAGCGATGGAGA CAGACCAC3' (SEQ ID NO: 42) |
| PpPP2C-1 | 5'CGGATGGATGAGATGA TGAAGGGAG3' (SEQ ID NO: 43) | 5'CACGACCACCATGGACG AAGCCTCCA3' (SEQ ID NO: 44) |
| PpPP2C-2 | 5'GGCTGTGCTCGGTAGA TTCTCTCGCA3' (SEQ ID NO: 45) | 5'CAGCCTCTTCGTTGGAC AAGTGCTC3' (SEQ ID NO: 46) |

Example 10

Engineering Stress-Tolerant Soybean Plants by Over-Expressing the PP2A-Z PP2A-3, PP2A-4, PP2C-1 or PP2C-2 Gene The constructs pBPSJYW023, pBPSSY007, pBPSJYW016, pBPSJYW017 and pBPSERG014 are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 µM acetosyringone. Bacterial cultures are incubated in this pre-induction medium for 2 hours at room temperature before use. The axes of soybean zygotic seed embryos at approximately 15% moisture content are imbibed for 2 hours at room temperature with the pre-induced *Agrobacterium* suspension culture. The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated during 4 weeks at 25° C., under 150 $\mu mol\, m^{-2}\, sec^{-1}$ and 12 hours photoperiod, Once the seedlings produce roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 $\mu mol\, m^{-2}\, sec^{-1}$ light intensity and 12 hours photoperiod for about 80 days.

The transgenic plants are then screened for their improved drought salt and/or cold tolerance according to the screening method described in Example 7 to demonstrate that transgene expression confers stress tolerance.

Example 11

Engineering Stress-Tolerant Rapeseed/Canola Plants by Over-Expressing the PP2A-2, PP2A-3, PP2A-4, PP2C-1 or PP2C-2 genes The constructs pBPSJYW023, pBPSSY007, pBPSJYW016, pBPSJYW017 and pBPSERG014 are used to transform rapeseed/canola as described below.

The method of plant transformation described herein is also applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period, the seeds lose approx. 85% of its water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved stress tolerance according to the screening method described in Example 7 demonstrating that transgene expression confers drought tolerance.

Example 12

Engineering Stress-Tolerant Corn Plants by Over-Expressing the PP2-2, PP2A-3, PP2A-4, PP2C-1 or PP2C-2 Genes The constructs pBPSJYW023, pBPSSY007, pBPSJYW016, pBPSJYW017 and pBPSERG014 are used to transform corn as described below.

Transformation of maize (*Zea Mays* L.) is performed with the method described by Ishida et al. 1996. Nature Biotch 14745-50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are then screened for their improved drought, salt and/or cold tolerance according to the screening method described in Example 7 demonstrating that transgene expression confers stress tolerance.

Example 13

Engineering Stress-Tolerant Wheat Plants by Over-Expressing the PP2A-2, PP2A-3, PP2A-4, PP2C-1 or PP2C-2 Genes The constructs pBPSJYW023, pBPSSY007, pBPSJYW016, pBPSJYW017 and pBPSERG014 are used to transform wheat as described below.

Transformation of wheat is performed with the method described by Ishida et al. 1996 Nature Biotch, 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7 demonstrating that transgene expression confers drought tolerance.

Example 14

Identification of Homologous and Heterologous Genes

Gene sequences can be used to identify homologous or heterologous genes from cDNA or genomic libraries. Homologous genes (e.g. full-length cDNA clones) can be isolated via nucleic acid hybridization using for example cDNA libraries. Depending on the abundance of the gene of interest 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. In aqueous solution hybridization and washing is performed at an ionic strength of 1 M NaCl and a temperature of 68° C. Hybridization probes are generated by e.g. radioactive ($^{32}P$) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10-20 amino acids) can be carried out by using synthetic radio labeled oligonucleotide probes. Radio labeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide Hybridization Solution:
6×SSC
0.01 M sodium phosphate
1 mM EDTA (pH 8)
0.5% SDS
100 µg/ml denatured salmon sperm DNA
0.1% nonfat dried milk During hybridization, temperature is lowered stepwise to 5-10° C. below the estimated oligonucleotide Tm or down to room temperature followed by washing steps and autoradiography. Washing is performed with low stringency such as 3 washing steps using 4×SSC. Further details are described by Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons.

Example 15

Identification of Homologous Genes by Screening Expression Libraries with Antibodies c-DNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994 BioTechniques 17:257-262. The antibody can than be used to screen expression cDNA libraries to identify homologous or heterologous genes via an immunological screening (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons).

Example 16

In Vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and *Salmonella*, p. 2277-2294, ASM: Washington.) Such strains are well known to those skilled in the art. The use of such strains is illustrated, for example, in Greener, A. and Callahan, M. (1994) *Strategies* 7: 32-34. Transfer of mutated DNA molecules into plants is preferably done after selection and testing in microorganisms. Transgenic plants are generated according to various examples within the exemplification of this document.

Example 17

In Vitro Analysis of the Function of *Physcomitrella* Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβ1, M., eds. (1983-1986) Methods of Enzymatic Analysis, $3^{rd}$ ed., vol. I-XII, Verlag Chemie: Weinheim; and Ullmann's Encyclopedia of Industrial Chemistry (1987) vol. A9, Enzymes. VCH: Weinheim, p. 352-363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) *EMBO J.* 14: 3895-3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B. Pores, Channels and Transporters, in Biomembranes, Molecular Structure and Function, pp. 85-137, 199-234 and 270-322, Springer: Heidelberg (1989).

Example 18

Purification of the Desired Product from Transformed Organisms

Recovery of the desired product from plant material (i.e., *Physcomitrella patens* or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, can be harvested from the culture by low-speed centrifugation, the cells can be lysed by standard techniques, such as mechanical force or sonification. Organs of plants can be separated mechanically from other tissue or organs. Following homogenization cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986). Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994 *Appl. Environ. Microbiol.* 60:133-140; Malakhova et al., 1996 *Biotekhnologiya* 11:27-32; and Schmidt et al., 1998 *Bioprocess Engineer.* 19:67-70. Ulmann's Encyclopedia of Industrial Chemistry, (1996) vol. A27, VCH: Weinheim, p. 89-90, p. 521-540, p. 540-547, p. 559-566, 575-581 and p. 581-587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

The invention claimed is:

1. A transgenic plant cell transformed by a polynucleotide encoding a polypeptide comprising amino acids 1 to 532 of SEQ ID NO:12.

2. The transgenic plant cell of claim 1, wherein the polynucleotide comprises nucleotides 1 to 2005 of SEQ ID NO:7.

3. The transgenic plant cell of claim 1, further described as a monocot.

4. The transgenic plant cell of claim 1, further described as a dicot.

5. The transgenic plant cell of claim 1, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass and forage crops.

6. The transgenic plant cell of claim 5, wherein the plant is maize.

7. The transgenic plant cell of claim 5, wherein the plant is soybean.

8. The transgenic plant cell of claim 5, wherein the plant is rapeseed or canola.

9. The transgenic plant cell of claim 5, wherein the plant is cotton.

10. An isolated polynucleotide encoding a polypeptide comprising amino acids 1 to 532 of SEQ ID NO:12.

11. The polynucleotide of claim 10, comprising nucleotides 1 to 2005 of SEQ ID NO:7.

12. A recombinant expression vector comprising an isolated polynucleotide encoding a polypeptide comprising amino acids 1 to 532 of SEQ ID NO:12.

13. The vector of claim 12, wherein the polynucleotide comprises nucleotides 1 to 2005 of SEQ ID NO:7.

14. A seed which is true breeding for a transgene comprising a polynucleotide encoding a polypeptide comprising amino acids 1 to 532 of SEQ ID NO:12.

15. The seed of claim 14, wherein the polynucleotide comprises nucleotides 1 to 2005 of SEQ ID NO:7.

16. A method of producing a transgenic plant comprising the steps of:
   a) transforming a plant cell with an expression vector comprising a polynucleotide encoding a polypeptide comprising amino acids 1 to 532 of SEQ ID NO:12; and
   b) generating from the plant cell a transgenic plant that expresses the polypeptide.

17. The method of claim 12, wherein the polynucleotide comprises nucleotides 1 to 2005 of SEQ ID NO:7.

* * * * *

SEQUENCE LISTING

<160> NUMBER OF SEQ ID NOS: 46

<210> SEQ ID NO 1
<211> LENGTH: 656
<212> TYPE: DNA
<213> ORGANISM: Physcomitrella patens

<400> SEQUENCE: 1

```
gcacgaggag gacaagtctt ccgaacccag cttagagtac tggttcaagt gtgtagacct      60
ggattgtgac gggatgatta tgctacgagg agatgcaata tttttacgag gagcaacttc     120
atcggatgga gtgcatggct caggagcctg ttcttttga ggatatcgtt tgtcaaatga     180
cagatatgat cggacctgct aatgaaggac ggttgacact tcgggactta aagcgatgca     240
aattatctgg aaacttcttc aatatccttt ttaacctcaa caaattcgta gcttttgaga     300
ctcgtgatcc tttccttatt cgtcaggaga gagggaccc gtcattaact gagtgggatc     360
gatttgcaca cattgagtac atccgacttt caatggaaga agatggcgag gatgcctcca     420
acggcagtgc tgaagtctgg gatgagcctg gttacgaagc ccccttttaa ccttctgttg     480
tccctcaaga tccaggcatt tgaatcatca gagcagagac ggacggcacg aagaattgcc     540
tgctggactt taagaaaac tggtctgtgc acccctttaa aggttgtcat ttatatcgta     600
aagcatcttg ttgagtgagc atcctgccta ggggaccctg tctctacttt aacatc        656
```

<210> SEQ ID NO 2
<211> LENGTH: 807
<212> TYPE: DNA
<213> ORGANISM: Physcomitrella patens

<400> SEQUENCE: 2

```
cggcacgagg aagcaggtta gaacctcaat gtggatcccg gagctagagg aaatgggagt      60
ttgctgacaa atagtatgtt gcttaatcca aagggcttgg caccacgtct atcatcaaac     120
ggaggacctg tgcacgagg catgccgtaa tcagccagga ctttgtattt cctcctggag     180
gcattccgtc acttcatctt ccctcggtag tagtttggag taacgaaacg acattagttg     240
cgagatgtag aagagtctac gcaaacgctc atgcatatca catcaactcc atatccaaca     300
acagcgattg tgagacatac atatctgcag atgatttgag aataaattta tggaaccttg     360
aagttagtga tcagagtttc aacattgttg acatcaaacc aacaaacatg gaagacctta     420
cagaggtgat aacgtctgca gagttccatc ctactcattg caatgtgtta gcatacagta     480
gcagcaaggg ctccattcga ctcattgata tgcgtcaatc agccttgtgt gatcgacact     540
ctaaagctgt tgaggaaga actggagccc atcctggatc caagatcctt tttttcacag     600
aaatccatag cttcaatttc tgacattaag tttgcaagag gcgatcggta cattctccag     660
```

-continued

```
tcggggacta catgyactct gaaactgtgg gatgtgaaca tggaatctgg tccctgtggc       720
acgtatttaa agtccacgag catttgcgac caaagcttcg tgatctctat gagaacgatt      780
cacctccgat aattgatgtg tccgggg                                           807
```

<210> SEQ ID NO 3
<211> LENGTH: 447
<212> TYPE: DNA
<213> ORGANISM: Physcomitrella patens

<400> SEQUENCE: 3

```
ggcacgagga agtatggaaa tgcgaatgtt tggaagtact tcacggatct gttcgactac       60
ctgcctctga cagctctcat tgagcacgag attttttgtc ttcatggtgg tctgtctcca     120
tcgctcgaca cattagatca catccgagcc ctagatcgta ttcaagaagt gccgcacgag     180
ggcccgatgt gtgatctact ctggtctgat ccagatgatc gttgtggatg ggtatttca     240 ccacgaggtg ccggttatac ttttggtcaa gatattgcag agcagttcaa tcataccaat     300
ggtctaagtt tggttgcacg tgctcaccag cttgtgatgg aaggatacaa ttggtgccag     360
gataaaaatg ttgtcacagt tttcagtgcc cccaattact gttaccgctg tgggaacatg     420
gccgccataa tgggagatag atgaaac                                          447
```

<210> SEQ ID NO 4
<211> LENGTH: 591
<212> TYPE: DNA
<213> ORGANISM: Physcomitrella patens

<400> SEQUENCE: 4

```
gcaccaggtt actgtggggc ctcgtcccccc ggaagagcat gttagctggg gttagagagc      60
tagggcagtg agtgccgatc attttttgcgt cacgcgtatc gatttgcaag ggcgaagtgc    120
acaagaggga tgggaattta tctttgctct ccaaagactg acaagacatc cgaagatgat    180
gagaatgccg agttacgcta tggtttatca gccatgcaag ggtggcgcga tagcatggag    240
gatgcacaca aagctatctt aaacgttgat aagaacacgt caacatcaat atttggcatc    300
tttgatggtc acggaggtaa attggtggca aaattttgtg caaagcactt acaccaagag    360
gttctgaagt ctgaagcgta cgctaaaggt gacttaaaag caagtttgga atattccttt    420
ttacggatgg atgagatgat gaagggagca agtgggtgga aagagcttca agtttggag    480 gaaacaagta gtcagcttga taaactcggt aatggaaata gctcctctaa tgcgagggag    540
gatgacgaaa gtgattattc ctatgctgtg ctaactgaaa gcaatgatag t              591
```

<210> SEQ ID NO 5
<211> LENGTH: 587
<212> TYPE: DNA
<213> ORGANISM: Physcomitrella patens
<220> FEATURE:
<221> NAME/KEY: modified_base
<222> LOCATION: (9)
<223> OTHER INFORMATION: a, t, c, g, other or unknown
<220> FEATURE:
<221> NAME/KEY: modified_base
<222> LOCATION: (283)
<223> OTHER INFORMATION: a, t, c, g, other or unknown

<400> SEQUENCE: 5

```
cggcacacng tttgtaccgc catttacaga aattgccacc caacatgggg gaatgtctag       60
tgaggttctt cagtcaagcc tttaagcaga ccgaggaggg gttttttggaa atcgtaaggg    120
```

```
attcatggct cacgaagccc cagattgctg ccgttggttc ctgttgcctg gtaggtgtgg    180
tgtgggagtg taagctgtac atcgccagcc tgggtgattc taaggctgtg ctcggtagat    240
tctctcgcaa tttgcaatca gtaattgcga cggagatatc ctnctgagca taacgccagt    300
gttgaggctg ttaggcagga cctgcaagct gcgcatcctg atgacccgcg cattgttgtg    360
ctgaggcacg gagtgtggcg tgtgaagggt ttgattcaag tctctcgatc cattggcgac    420
gtttatctga agaaggctga gttcaaccgt gagcctctaa tcggccggtt ccgcctgcca    480
gagccgctcc agagacccgt catgagcgcc gagccggaca tccgagtaat cgatctgacc    540
ccagatgtgg agttgtgatt tgcatcaga tgggttgtgg gagcact                   587
```

<210> SEQ ID NO 6
<211> LENGTH: 2559
<212> TYPE: DNA
<213> ORGANISM: Physcomitrella patens

<400> SEQUENCE: 6

```
atcccgggca tcgggaaaga cggtgtgtgt gtgtgtgtgt gtttgcttgc ttgcatgcat     60 tgtgggggt acccagatca tgcttcaggg aggtttggag tgcgcccaat ggagcccttg    120
acgttggccg tggcagatct ggaccccgat ctgcttcaac tccctgcgga tttcaccccc    180
tttgcttctc cttcatcgtc atcgcctgct tctgtgggga ttagcaacaa gcttggaggt    240
gtttgtaggt tgcacttgga ggagctttac gcgcaatgga tttcgctgcc cgacacgcag    300
cgtctggtta cgaatttgtt ggaagaagca aaggaggag ctggacaccc aaatgttggc    360
ctatcacttt tgccaggtca tctatctgga gccgcaggaa gcactccccc gttgcctcct    420
cggagctctg gttcaccaat gtctcccagg tcgccttttca gcagacgtat gggaactagc    480
cacctcatgc gggactctcc gttgaagaaa agtagcgaac ctgtgcgaga tcataccc     540 cagttctatt ttccgaatgg ccccccgcca tcgaaggata ccattgagtc gtgcatggct    600
cgcgtaaacc aaatattcgg agctcatcca gaaggtttac ctgcatcagc atttgcaacc    660
attactaagg atgtatgcaa actaccgtcc ttcttctcca tggctttatt caaaaagatt    720
gacatcaata atacaggctt ggttacaagg acaagttcg tagaatactg ggtggaccaa    780
aacatgctgg ccatggacac tgcaactcgc gtcttcactg tgttgaagca acccgacaag    840
aattttctga cagaggaaga ttttaggccc gttttacgag aattgttgtt gacgcatcgc    900
ggtttggaat tctccatga cacccccggag tttcaagaca gatatgctga aactgtaata    960
tacagaatat tctaccatgt aaatagagct gggaatggtc ggctacaact tagagagtta   1020
aagcggagta atttaattgc tgctcttcag caagtggatg aagaggaaga catcaacaaa   1080
gtgttacgtt acttctcata tgaacatttt tatgtcatat attgcaagtt ctgggagctg   1140
gattcagatc acgatttttt aatagacaaa gatgatctcc ttcgatatgg aaatcatgct   1200
ctcacctacc gaatcgtaga gcgtatcttt tcccaggttc aagaaagtt caccagcaaa   1260 gtagctggaa agatgggtta tgaagacttc gtatggttta ttctttcaga agaggacaag   1320
tcttccgaac ccagcttaga gtactggttc aagtgtgtag actggattg tgacgggatg   1380 attatactaa atgagatgca atattttac gaggagcaac ttcatcggat ggagtgcatg   1440
gctcaggagc ctgttctttt tgaggatatc gtttgtcaaa tgacagatat gatcggacct   1500
gctaatgaag acggttgac acttcgggac ttaaagcgat gcaaattatc tggaaacttc   1560
ttcaatatcc tttttaacct caacaaattc gtagcttttg agactcgtga tccttttcctt   1620 attcgtcagg agagagagga cccgtcatta actgagtggg atcgatttgc acacattgag   1680
```

```
tacatccgac tttcaatgga agaagatggc gaggatgcct ccaacggcag tgctgaagtc    1740
tgggatgagc ctggttacga agccccttt taaccttctg ttgtccctca agatccaggc    1800
atttgaatca tcagagcaga gacgacggca acgaagaatt gcctgctgga cttttaagaa    1860
aactggtctg tgcaacccct taaaggttgt ccatttatat cgtaaagcat cttgtttgag    1920
tgagcatcct gcctagggga accctgtctc tactttaaaa tcagacaatg catgtgacat    1980
ttgtacagtt cacaaatggc agcatttatc tatttaggaa gtccttcaac attatatctt    2040
tcaggtctcc agctcgccat ttacgggtgc tactgtaact cgagtccttg tgcaagaatc    2100
atgaagaata ctgagcatgg cgacgtccaa aacttcgaga caacgtcaaa gaactacttg    2160
accggtctct caacaagttc tgttacttaa gtgcacagca ctgggggtagc cctcttgctt    2220 tcaaaatcac tgtgtgtgac actgtagcta ctacttcagg gaaattgatg ttgggcattc    2280
taggccttct gagctttttt tgcaggtctt tttgatggtc tccgtcacgt tatttgttta    2340
ggaatgaagc agcctgccca ggatagtgat gtagacatgg tcccgtttct gatcttctca    2400
atcaggctta accatgcagt aattaagcag gtaggcacag tgtgctcaac acgtaatccc    2460
cttcccacac tagtcttctc tgtagactct ttatttcagc ttttgatccg gaacttaaag    2520
cttttgactg gttcagcccg aggctggtag cgttaacgc                          2559

<210> SEQ ID NO 7
<211> LENGTH: 2005
<212> TYPE: DNA
<213> ORGANISM: Physcomitrella patens

<400> SEQUENCE: 7
atcccgggtg gtggtggcgg tgaagttatt acccgagagc ttcgacagct tcacgcatgt      60
ttgcgattgc acgcaaggac gcaactggct ccgtagttgt aatgaatgga ttcaccgcga     120
tgcaagcttc tcaacgagcc gttggaagct tcgtgtggtg gagtgtggaa actgccggag     180
ctccgtaacc atgcgggggtt catggaagtg gtggctgcca attcggaggc ggatttcaat    240
gtggtagagt ttggacttag agttttgtag gaggaggggt tgaagtgtgg gccaagtgtt     300
ggggctcctg aaacagggga aaagaaaaag agacgacgac gccggagatt ggagattgag     360
gtgtgtgtgt gtgtgtttgt ggttagttta gcggtttgaa gtgatgatca gtggtgcaag     420
cggggcaccc gctgggcccc agttcccac tgctactggt tctgttgctg cgccattgcc      480
cgcgttggag tggaaattct cgcaggtttt cggcgagcgt gccatcggag aggaagtgca     540
agaagttgat attatctcgg ctattgagtt tgataagact ggagaacatt tggcgactgg     600
cgacagagga ggacgcgttg acttttttga gagaacagat ggcaaagatc aaaggacacg     660
gagagagttg gaaagagctg attctgcggg gtccaggcat cctgaatatc gatactctac     720
cgagtttcaa agtcatgaac cagagtttga ttacttgaag agtttggaaa tagaggagaa     780
gatcaataaa attagatggt gtcagactgc caacgccgct cagttcttaa tttctacgaa     840
tgacaaaacc attaaattat ggaaggtgac tgaaaagaaa gtgaagcaag tcaagaacct     900
gaatgtggat cctggagcca gagggaatgg aaacccattg tcgaataaca tgatgctcaa     960
tccaaagggt tttgcaccac ggttgtcgat aatggagtt gccgcgaacc gatctacgcc     1020
tgccatcagc cctgactttg tatttcctcc tggaggcatt ccgtctcttc atcttccctc    1080
ggtatggagt aacagacgg cattagttgc gagatgtaga agagcctacg caaacgctca     1140
tgcatatcat atcaactcca tatctaacaa cagcgattgt gagacataca tctctgcaga    1200
```

```
tgatttgaga ataaatttat ggaatcttga agttagtgat cagagtttca atattgttga   1260
catcaaacca acaaacatgg aagaccttac agaggtgata acgtctgcag agttccatcc   1320
ttctcattgc aatgtgttag catacagtag cagcaagggc tctattcgac tcattgatat   1380
gcgtcaatca gccttgtgtg atcgacattc aaagctgttt gaggagactg agcatgctgg   1440
atcaagatcc ttttttacag aaatcatagc ttctatttct gatattaagt ttgcgagagg   1500
cggtcggtac attctgagtc gggactacat gactctgaaa ttgtgggatg tgaacatgga   1560
atcttcccct gtggccgtat ttaaagtcca cgagtatttg cgtccaaagc tttgtgatct   1620
ctatgagaac gactccatct tcgacaagtt tgaatgttgt cttagtgggg atggcatgcg   1680
tgtggcaact ggttcctaca gcaacttgtt ccgggtgttt ggggccgcta ccggaagtga   1740
ggaagcgtca accttggaag ctagcaagac tccaaacagg cgtatcgtga cacctccctc   1800
aaaagctgga agtcgactag ccaatcttgc tcgtggtcgg cgtgataacc gtcgaggtgg   1860
agaaagccca ggtatagatt tgaatggggg agtgcaagat ttcacatcaa gcttttgca   1920 cttagcatgg catccagcag cgaatgtgat cgctttcgcg ctagcgcgtt gctcgctgca   1980
tccaacagct tgtacatgtt aacgc                                          2005

<210> SEQ ID NO 8
<211> LENGTH: 1365
<212> TYPE: DNA
<213> ORGANISM: Physcomitrella patens

<400> SEQUENCE: 8
ggcgttaacg cgcggaggag agcggatcgg ttagggtttg gtgccagggg ggagggcaga     60
ggttgggaca atgccgtcat atgcagatgt agaccggcag atagagcagc tgtcggagtg    120
caagccgttg tcggagttgg aggtgaagaa cctatgtgat caagctcgga cgatcttggt    180
ggaggagtgg aacgtgcagc ccgtgaagtg tcctgtcacg gtttgcggtg acatccatgg    240
ccagtttcat gatctcatcg agcttttccg cataggaggc aaggcgcccg cacgaaacta    300
cttgttcatg ggcgactatg tggatcgtgg atattattct gtcgagactg tgtcgctctt    360
agtggccctg aaggtgcggt atagggatag gatcacaatc ttgcgaggga accacgagag    420
caggcagatt acgcaagtat atggtttcta tgatgaatgc ctgcggaagt atggaaatgc    480
gaatgtttgg aagtacttca cggatctgtt cgactacctg cctctgacag ctctcattga    540
gcacgagatt ttttgtcttc atggtggtct gtctccatcg ctcgacacat tagatcacat    600
ccgagcccta gatcgtattc aagaagtgcc gcacgagggc ccgatgtgtg atctactctg    660
gtctgatcca gatgatcgtt gtggatgggg catttcacca cgaggtgccg gttatacttt    720
tggtcaagat attgcagagc agttcaatca taccaatggc taagtttgg ttgcacgtgc    780 tcaccagctt gtgatggaag atacaattg tgccaggat aaaaatgttg tcacagtttt    840
cagtgccccc aattactgtt accgctgtgg gaacatggcc gccataatgg agatagatga    900
aacaatgaat cggtcttttc ttcagttcga accagcaccg cggcaaagtg aaccagatgt    960
gacgcggaag actcctgatt actttctgta aacatggcct atacatggta ccttttactt   1020
actgaattgt tctgtatagt caccttccat ggaagcagtt tgcccctgaa tgaagatact   1080
ccctcatgat ctagtagtat gaagttatct tctttgaagt gtttgttccc ttttttagta   1140
cttgctcctc tgttcattca taaagttgcc ttcagaacaa ctgagatgtt gtgaatgtaa   1200
ctgcgacaag aggagcagtg tcaatggttg caagggttat agtgattagg gaaagaaggt   1260
agcacatgtt acttcaaatc gatcagagac ttctatggaa aagatgacga tggtggaaac   1320
```

```
aacgttcatc tccacaccta ctgtatatgg catgctcgag ctcgc            1365

<210> SEQ ID NO 9
<211> LENGTH: 1346
<212> TYPE: DNA
<213> ORGANISM: Physcomitrella patens

<400> SEQUENCE: 9
gcgatatcga tttgcaaggg cgaagtgcac aagagggatg ggaatttatc tttgctctcc     60
aaagactgac aagacatccg aagatgatga gaatgccgag ttacgctatg gtttatcagc    120
catgcaaggg tggcgcgata gcatggagga tgcacacaaa gctatcttaa acgttgataa    180
gaacacgtca acatcaatat ttggcatctt tgatggtcac ggaggtaaat tggtggcaaa    240 atttttgtgca aagcacttac accaagaggt tctgaagtct gaagcgtacg ctaaaggtga    300
cttaaaagca agtttggaat attccttttt acggatggat gagatgatga agggagcaag    360
tgggtggaaa gagcttcaaa gtttggagga aacaagtagt cagcttgata aactcggtaa    420
tggaaatagc tcctctaatg cgagggagga tgacgaaagt gattattcct atgctgtgct    480
aactgaaagc aatgatagta acttggccac taaaaagcat aaatattcag atttccaggg    540
tcccatttat gggagtactg cagtggtggc tctgattcgt ggcaataaac tgttcgtcgc    600
aaacgctgga gactctcgct gcataatgtc tcgacgtggc gaggctgtaa atctctcgat    660
tgatcacaaa cccaacctag agcatgagag gaaaaggata gagagtgctg gaggcttcgt    720
ccatggtggt cgtgttaacg gtagtctaaa tcttacaaga gcaataggggg acatggaatt    780 caagggtcga cctgatttgc cacctgacaa gcaagtagtg acgtgctgtc ccgatgttgt    840
cgaagttgac cttggacccg gggatgaatt tatcgtgctg gcctgtgatg gaatatggga    900
tgttatgtct agtcaagctg tcgtggactt cgttaaatca agattaccta ccaccaaaac    960
tctatcatct ttgtgtgagg agatactgga ttactgcttg tccccaacca cccgccagca   1020
agaaggatgt gataacatga gcatcattat agtccaacca aagcaatcgg gagttgcagc   1080
atcttcttcc acagattgac gttgatgacc ttcgtcggac gctggagctc aaaactcatt   1140
gtggacttca acttctgagt tcaaagttcc ttgtagactt cttgtcatgt ccaacttcta   1200
cctaatttcg aatttcaaaa gacttaaata taaacctaga tataggctga tcataaaatt   1260
tcgggtcaaa ggcgttatgg tcttctattc aaatataagg tgaattaatg ctaaaactgg   1320 gagttgccctt ctgccttcga tatcgc                                        1346

<210> SEQ ID NO 10
<211> LENGTH: 1410
<212> TYPE: DNA
<213> ORGANISM: Physcomitrella patens

<400> SEQUENCE: 10
atcccgggcg tggaaggaga gggaatgtgg aggaaagagt ggagttatta tttgtcagtc     60
gaatgtacag gaagaagcga aaaggatatg gagtggaaat atgaagaagc tggttgaaga    120
aggacgtctg agagatggta gagtgggtaa tgaagatgtt gatggcatgt tggcgtccgg    180
tgcaaaaata cacgcacctg ggggaggaga atggagataa ccacgaccca ctgctgtggc    240
acaaagattt gggtgatcat gccgcaggac agttttctat tgccgcagtt caggcgaatg    300
ctatcttgga ggacatggtc caagtggaaa ctgaccgtt tggtacctttt gttggggtgt    360 acgatggcca tggtggcccg gaagcttctc gttacgtcaa tgacagtttg taccgccatt    420
```

-continued

```
tacagaaatt tgccacccaa catgggggaa tgtctagtga ggttcttcag caagccttta    480
agcagaccga ggaggggttt ttggaaatcg taagggattc atggctcacg aagccccaga    540
ttgctgccgt tggttcctgt tgcctggtag gtgtggtgtg ggagtgtaag ctgtacatcg    600
ccagcctggg tgattctaag gctgtgctcg gtagattctc tcgcaatttg caatcagtaa    660
ttgcgacgga gatatccact gagcataacg ccagtgttga ggctgttagg caggacctgc    720
aagctgcgca tcctgatgac ccgcgcattg ttgtgctgag gcacggagtg tggcgtgtga    780 aggggtttgat tcaagtctct cgatccattg gcgacgttta tctgaagaag gctgagttca    840
accgtgagcc tctaatcggc cggttccgcc tgccagagcc gctccagaga cccgtcatga    900
gcgccgagcc ggacatccga gtaatcgatc tgaccccaga tgtggagttt gtgattttg     960 catcagatgg gttgtgggag cacttgtcca accaagaggc tgtggatatt gttcacaaat    1020
acccgcgcgc tggcatcgcc aggcagctca ttcgatacgc tcttcatgaa gcggccaaga    1080
agcgagagat gcggtactcg gatctgaaga agatcgagcg tggtatccgg agacactttc    1140
atgacgacat cacagtggta gtcgtcttct tagatcataa tttggttagc aatggtagtg    1200
gtatctcgca tcacatttct gtgaaaggtg gagttgacaa accttcttga aaaggggtcg    1260
taggtactct ccatggtatc ttgcaggttt tgtcacatga aacttccccc tttcgcacga    1320
tggggtagaa gtgattgctc ctttgaagct acacctccct gcaacccaat cgtctgtcga    1380
acctgaagct agacacccac aggagcttgc                                     1410
```

<210> SEQ ID NO 11
<211> LENGTH: 572
<212> TYPE: PRT
<213> ORGANISM: Physcomitrella patens

<400> SEQUENCE: 11

```
Met His Cys Gly Gly Tyr Pro Asp His Ala Ser Gly Arg Phe Gly Val
  1               5                  10                  15

Arg Pro Met Glu Pro Leu Thr Leu Ala Val Ala Asp Leu Asp Pro Asp
             20                  25                  30

Leu Leu Gln Leu Pro Ala Asp Phe Thr Pro Phe Ala Ser Pro Ser Ser
         35                  40                  45

Ser Ser Pro Ala Ser Val Gly Val Ser Asn Lys Leu Gly Gly Val Cys
     50                  55                  60

Arg Leu His Leu Glu Glu Leu Tyr Ala Gln Trp Ile Ser Leu Pro Asp
 65                  70                  75                  80

Thr Gln Arg Leu Val Thr Asn Leu Leu Glu Glu Ala Lys Gly Gly Ala
                 85                  90                  95

Gly His Pro Asn Val Gly Leu Ser Leu Leu Pro Gly His Leu Ser Gly
            100                 105                 110

Ala Ala Gly Ser Thr Pro Pro Leu Pro Pro Arg Ser Ser Gly Ser Pro
        115                 120                 125

Met Ser Pro Arg Ser Pro Phe Ser Arg Arg Met Gly Thr Ser His Leu
    130                 135                 140

Met Arg Asp Ser Pro Leu Lys Lys Ser Ser Glu Pro Val Arg Glu Ile
145                 150                 155                 160

Ile Pro Gln Phe Tyr Phe Pro Asn Gly Pro Pro Ser Lys Asp Thr
                165                 170                 175

Ile Glu Ser Cys Met Ala Arg Val Asn Gln Ile Phe Gly Ala His Pro
            180                 185                 190

Glu Gly Leu Pro Ala Ser Ala Phe Ala Thr Ile Thr Lys Asp Val Cys
```

```
            195                 200                 205
Lys Leu Pro Ser Phe Phe Ser Met Ala Leu Phe Lys Lys Ile Asp Ile
        210                 215                 220

Asn Asn Thr Gly Leu Val Thr Arg Asp Lys Phe Val Glu Tyr Trp Val
225                 230                 235                 240

Asp Gln Asn Met Leu Ala Met Asp Thr Ala Thr Arg Val Phe Thr Val
            245                 250                 255

Leu Lys Gln Pro Asp Lys Asn Phe Leu Arg Gln Glu Asp Phe Arg Pro
        260                 265                 270

Val Leu Arg Glu Leu Leu Thr His Arg Gly Leu Glu Phe Leu His
        275                 280                 285

Asp Thr Pro Glu Phe Gln Asp Arg Tyr Ala Glu Thr Val Ile Tyr Arg
        290                 295                 300

Ile Phe Tyr His Val Asn Arg Ala Gly Asn Gly Arg Leu Gln Leu Arg
305                 310                 315                 320

Glu Leu Lys Arg Ser Asn Leu Ile Ala Ala Leu Gln Gln Val Asp Glu
            325                 330                 335

Glu Glu Asp Ile Asn Lys Val Leu Arg Tyr Phe Ser Tyr Glu His Phe
            340                 345                 350

Tyr Val Ile Tyr Cys Lys Phe Trp Glu Leu Asp Ser Asp His Asp Phe
            355                 360                 365

Leu Ile Asp Lys Asp Leu Leu Arg Tyr Gly Asn His Ala Leu Thr
        370                 375                 380

Tyr Arg Ile Val Glu Arg Ile Phe Ser Gln Val Pro Arg Lys Phe Thr
385                 390                 395                 400

Ser Lys Val Ala Gly Lys Met Gly Tyr Glu Asp Phe Val Trp Phe Ile
            405                 410                 415

Leu Ser Glu Glu Asp Lys Ser Ser Glu Pro Ser Leu Glu Tyr Trp Phe
            420                 425                 430

Lys Cys Val Asp Leu Asp Cys Asp Gly Met Ile Ile Leu Asn Glu Met
            435                 440                 445

Gln Tyr Phe Tyr Glu Glu Gln Leu His Arg Met Glu Cys Met Ala Gln
        450                 455                 460

Glu Pro Val Leu Phe Glu Asp Ile Val Cys Gln Met Thr Asp Met Ile
465                 470                 475                 480

Gly Pro Ala Asn Glu Gly Arg Leu Thr Leu Arg Asp Leu Lys Arg Cys
            485                 490                 495

Lys Leu Ser Gly Asn Phe Phe Asn Ile Leu Phe Asn Leu Asn Lys Phe
            500                 505                 510

Val Ala Phe Glu Thr Arg Asp Pro Phe Leu Ile Arg Gln Glu Arg Glu
            515                 520                 525

Asp Pro Ser Leu Thr Glu Trp Asp Arg Phe Ala His Ile Glu Tyr Ile
        530                 535                 540

Arg Leu Ser Met Glu Glu Asp Gly Glu Asp Ala Ser Asn Gly Ser Ala
545                 550                 555                 560

Glu Val Trp Asp Glu Pro Gly Tyr Glu Ala Pro Phe
            565                 570

<210> SEQ ID NO 12
<211> LENGTH: 532
<212> TYPE: PRT
<213> ORGANISM: Physcomitrella patens

<400> SEQUENCE: 12
```

-continued

```
Met Ile Ser Gly Ala Ser Gly Ala Pro Ala Gly Ala Pro Val Pro Thr
1               5                   10                  15

Ala Thr Gly Ser Val Ala Ala Pro Leu Pro Ala Leu Glu Trp Lys Phe
            20                  25                  30

Ser Gln Val Phe Gly Glu Arg Ala Ile Gly Glu Val Gln Glu Val
        35                  40                  45

Asp Ile Ile Ser Ala Ile Glu Phe Asp Lys Thr Gly Glu His Leu Ala
        50                  55                  60

Thr Gly Asp Arg Gly Gly Arg Val Val Leu Phe Glu Arg Thr Asp Gly
65                  70                  75                  80

Lys Asp Gln Arg Thr Arg Arg Glu Leu Glu Arg Ala Asp Ser Ala Gly
                85                  90                  95

Ser Arg His Pro Glu Tyr Arg Tyr Ser Thr Glu Phe Gln Ser His Glu
            100                 105                 110

Pro Glu Phe Asp Tyr Leu Lys Ser Leu Glu Ile Glu Glu Lys Ile Asn
        115                 120                 125

Lys Ile Arg Trp Cys Gln Thr Ala Asn Ala Ala Gln Phe Leu Ile Ser
        130                 135                 140

Thr Asn Asp Lys Thr Ile Lys Leu Trp Lys Val Thr Glu Lys Lys Val
145                 150                 155                 160

Lys Gln Val Lys Asn Leu Asn Val Asp Pro Gly Ala Arg Gly Asn Gly
                165                 170                 175

Asn Pro Leu Ser Asn Asn Met Met Leu Asn Pro Lys Gly Phe Ala Pro
            180                 185                 190

Arg Leu Ser Met Asn Gly Val Ala Ala Asn Arg Ser Thr Pro Ala Ile
        195                 200                 205

Ser Pro Asp Phe Val Phe Pro Pro Gly Gly Ile Pro Ser Leu His Leu
        210                 215                 220

Pro Ser Val Trp Ser Asn Glu Thr Ala Leu Val Ala Arg Cys Arg Arg
225                 230                 235                 240

Ala Tyr Ala Asn Ala His Ala Tyr His Ile Asn Ser Ile Ser Asn Asn
                245                 250                 255

Ser Asp Cys Glu Thr Tyr Ile Ser Ala Asp Leu Arg Ile Asn Leu
            260                 265                 270

Trp Asn Leu Glu Val Ser Asp Gln Ser Phe Asn Ile Val Asp Ile Lys
        275                 280                 285

Pro Thr Asn Met Glu Asp Leu Thr Glu Val Ile Thr Ser Ala Glu Phe
        290                 295                 300

His Pro Ser His Cys Asn Val Leu Ala Tyr Ser Ser Lys Gly Ser
305                 310                 315                 320

Ile Arg Leu Ile Asp Met Arg Gln Ser Ala Leu Cys Asp Arg His Ser
                325                 330                 335

Lys Leu Phe Glu Glu Thr Glu His Ala Gly Ser Arg Ser Phe Phe Thr
            340                 345                 350

Glu Ile Ile Ala Ser Ile Ser Asp Ile Lys Phe Ala Arg Gly Gly Arg
        355                 360                 365

Tyr Ile Leu Ser Arg Asp Tyr Met Thr Leu Lys Leu Trp Asp Val Asn
        370                 375                 380

Met Glu Ser Ser Pro Val Ala Val Phe Lys Val His Glu Tyr Leu Arg
385                 390                 395                 400

Pro Lys Leu Cys Asp Leu Tyr Glu Asn Asp Ser Ile Phe Asp Lys Phe
                405                 410                 415

Glu Cys Cys Leu Ser Gly Asp Gly Met Arg Val Ala Thr Gly Ser Tyr
```

```
                   420                 425                 430
Ser Asn Leu Phe Arg Val Phe Gly Ala Ala Thr Gly Ser Glu Glu Ala
        435                 440                 445

Ser Thr Leu Glu Ala Ser Lys Thr Pro Asn Arg Arg Ile Val Thr Pro
    450                 455                 460

Pro Ser Lys Ala Gly Ser Arg Leu Ala Asn Leu Ala Arg Gly Arg Arg
465                 470                 475                 480

Asp Asn Arg Arg Gly Gly Glu Ser Pro Gly Ile Asp Leu Asn Gly Gly
                485                 490                 495

Val Gln Asp Phe Thr Ser Lys Leu Leu His Leu Ala Trp His Pro Ala
            500                 505                 510

Ala Asn Val Ile Ala Phe Ala Leu Ala Arg Cys Ser Leu His Pro Thr
        515                 520                 525

Ala Cys Thr Cys
    530

<210> SEQ ID NO 13
<211> LENGTH: 306
<212> TYPE: PRT
<213> ORGANISM: Physcomitrella patens

<400> SEQUENCE: 13

Met Pro Ser Tyr Ala Asp Val Asp Arg Gln Ile Glu Gln Leu Ser Glu
  1               5                  10                  15

Cys Lys Pro Leu Ser Glu Leu Glu Val Lys Asn Leu Cys Asp Gln Ala
             20                  25                  30

Arg Thr Ile Leu Val Glu Glu Trp Asn Val Gln Pro Val Lys Cys Pro
         35                  40                  45

Val Thr Val Cys Gly Asp Ile His Gly Gln Phe His Asp Leu Ile Glu
     50                  55                  60

Leu Phe Arg Ile Gly Gly Lys Ala Pro Asp Thr Asn Tyr Leu Phe Met
 65                  70                  75                  80

Gly Asp Tyr Val Asp Arg Gly Tyr Tyr Ser Val Glu Thr Val Ser Leu
                 85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys Tyr Phe Thr
    130                 135                 140

Asp Leu Phe Asp Tyr Leu Pro Leu Thr Ala Leu Ile Glu His Glu Ile
145                 150                 155                 160

Phe Cys Leu His Gly Gly Leu Ser Pro Ser Leu Asp Thr Leu Asp His
                165                 170                 175

Ile Arg Ala Leu Asp Arg Ile Gln Glu Val Pro His Glu Gly Pro Met
            180                 185                 190

Cys Asp Leu Leu Trp Ser Asp Pro Asp Asp Arg Cys Gly Trp Gly Ile
        195                 200                 205

Ser Pro Arg Gly Ala Gly Tyr Thr Phe Gly Gln Asp Ile Ala Glu Gln
    210                 215                 220

Phe Asn His Thr Asn Gly Leu Ser Leu Val Ala Arg Ala His Gln Leu
225                 230                 235                 240

Val Met Glu Gly Tyr Asn Trp Cys Gln Asp Lys Asn Val Val Thr Val
                245                 250                 255
```

```
Phe Ser Ala Pro Asn Tyr Cys Tyr Arg Cys Gly Asn Met Ala Ala Ile
            260                 265                 270

Met Glu Ile Asp Glu Thr Met Asn Arg Ser Phe Leu Gln Phe Glu Pro
        275                 280                 285

Ala Pro Arg Gln Ser Glu Pro Asp Val Thr Arg Lys Thr Pro Asp Tyr
    290                 295                 300

Phe Leu
305
```

<210> SEQ ID NO 14
<211> LENGTH: 353
<212> TYPE: PRT
<213> ORGANISM: Physcomitrella patens

<400> SEQUENCE: 14

```
Met Gly Ile Tyr Leu Cys Ser Pro Lys Thr Asp Lys Thr Ser Glu Asp
  1               5                  10                  15

Asp Glu Asn Ala Glu Leu Arg Tyr Gly Leu Ser Ala Met Gln Gly Trp
             20                  25                  30

Arg Asp Ser Met Glu Asp Ala His Lys Ala Ile Leu Asn Val Asp Lys
         35                  40                  45

Asn Thr Ser Thr Ser Ile Phe Gly Ile Phe Asp Gly His Gly Gly Lys
     50                  55                  60

Leu Val Ala Lys Phe Cys Ala Lys His Leu His Gln Glu Val Leu Lys
 65                  70                  75                  80

Ser Glu Ala Tyr Ala Lys Gly Asp Leu Lys Ala Ser Leu Glu Tyr Ser
                 85                  90                  95

Phe Leu Arg Met Asp Glu Met Met Lys Gly Ala Ser Gly Trp Lys Glu
            100                 105                 110

Leu Gln Ser Leu Glu Glu Thr Ser Ser Gln Leu Asp Lys Leu Gly Asn
        115                 120                 125

Gly Asn Ser Ser Asn Ala Arg Glu Asp Asp Glu Ser Asp Tyr Ser
    130                 135                 140

Tyr Ala Val Leu Thr Glu Ser Asn Asp Ser Asn Leu Ala Thr Lys Lys
145                 150                 155                 160

His Lys Tyr Ser Asp Phe Gln Gly Pro Ile Tyr Gly Ser Thr Ala Val
                165                 170                 175

Val Ala Leu Ile Arg Gly Asn Lys Leu Phe Val Ala Asn Ala Gly Asp
            180                 185                 190

Ser Arg Cys Ile Met Ser Arg Arg Gly Glu Ala Val Asn Leu Ser Ile
        195                 200                 205

Asp His Lys Pro Asn Leu Glu His Glu Arg Lys Arg Ile Glu Ser Ala
    210                 215                 220

Gly Gly Phe Val His Gly Gly Arg Val Asn Gly Ser Leu Asn Leu Thr
225                 230                 235                 240

Arg Ala Ile Gly Asp Met Glu Phe Lys Gly Arg Pro Asp Leu Pro Pro
                245                 250                 255

Asp Lys Gln Val Val Thr Cys Cys Pro Asp Val Glu Val Asp Leu
            260                 265                 270

Gly Pro Gly Asp Glu Phe Ile Val Leu Ala Cys Asp Gly Ile Trp Asp
        275                 280                 285

Val Met Ser Ser Gln Ala Val Val Asp Phe Val Lys Ser Arg Leu Pro
    290                 295                 300

Thr Thr Lys Thr Leu Ser Ser Leu Cys Glu Glu Ile Leu Asp Tyr Cys
305                 310                 315                 320
```

```
Leu Ser Pro Thr Thr Arg Gln Gln Glu Gly Cys Asp Asn Met Ser Ile
                325                 330                 335
Ile Ile Val Gln Pro Lys Gln Ser Gly Val Ala Ala Ser Ser Ser Thr
            340                 345                 350
Asp

<210> SEQ ID NO 15
<211> LENGTH: 371
<212> TYPE: PRT
<213> ORGANISM: Physcomitrella patens

<400> SEQUENCE: 15

Met Val Glu Trp Val Met Lys Met Leu Met Ala Cys Trp Arg Pro Val
 1               5                  10                  15
Gln Lys Tyr Thr His Leu Gly Glu Glu Asn Gly Asp Asn His Asp Pro
                20                  25                  30
Leu Leu Trp His Lys Asp Leu Gly Asp His Ala Ala Gly Gln Phe Ser
            35                  40                  45
Ile Ala Ala Val Gln Ala Asn Ala Ile Leu Glu Asp Met Val Gln Val
        50                  55                  60
Glu Thr Gly Pro Phe Gly Thr Phe Val Gly Val Tyr Asp Gly His Gly
 65                  70                  75                  80
Gly Pro Glu Ala Ser Arg Tyr Val Asn Asp Ser Leu Tyr Arg His Leu
                 85                  90                  95
Gln Lys Phe Ala Thr Gln His Gly Gly Met Ser Ser Glu Val Leu Gln
            100                 105                 110
Gln Ala Phe Lys Gln Thr Glu Glu Gly Phe Leu Glu Ile Val Arg Asp
        115                 120                 125
Ser Trp Leu Thr Lys Pro Gln Ile Ala Ala Val Gly Ser Cys Cys Leu
130                 135                 140
Val Gly Val Val Trp Glu Cys Lys Leu Tyr Ile Ala Ser Leu Gly Asp
145                 150                 155                 160
Ser Lys Ala Val Leu Gly Arg Phe Ser Arg Asn Leu Gln Ser Val Ile
                165                 170                 175
Ala Thr Glu Ile Ser Thr Glu His Asn Ala Ser Val Glu Ala Val Arg
            180                 185                 190
Gln Asp Leu Gln Ala Ala His Pro Asp Asp Pro Arg Ile Val Val Leu
        195                 200                 205
Arg His Gly Val Trp Arg Val Lys Gly Leu Ile Gln Val Ser Arg Ser
210                 215                 220
Ile Gly Asp Val Tyr Leu Lys Lys Ala Glu Phe Asn Arg Glu Pro Leu
225                 230                 235                 240
Ile Gly Arg Phe Arg Leu Pro Glu Pro Leu Gln Arg Pro Val Met Ser
                245                 250                 255
Ala Glu Pro Asp Ile Arg Val Ile Asp Leu Thr Pro Asp Val Glu Phe
            260                 265                 270
Val Ile Phe Ala Ser Asp Gly Leu Trp Glu His Leu Ser Asn Gln Glu
        275                 280                 285
Ala Val Asp Ile Val His Lys Tyr Pro Arg Ala Gly Ile Ala Arg Gln
    290                 295                 300
Leu Ile Arg Tyr Ala Leu His Glu Ala Ala Lys Lys Arg Glu Met Arg
305                 310                 315                 320
Tyr Ser Asp Leu Lys Lys Ile Glu Arg Gly Ile Arg Arg His Phe His
                325                 330                 335
```

```
Asp Asp Ile Thr Val Val Val Phe Leu Asp His Asn Leu Val Ser
            340                 345                 350

Asn Gly Ser Gly Ile Ser His His Ile Ser Val Lys Gly Gly Val Asp
        355                 360                 365

Lys Pro Ser
    370

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 16
caggaaacag ctatgacc                                              18

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 17
ctaaagggaa caaaagctg                                             19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 18
tgtaaaacga cggccagt                                              18

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 19
ctgccgttgg aggcatcctc gccatc                                     26

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 20
atcccgggca tcgggaagac ggtgtgtgtg tgtg                            34

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 21
```

```
gcgttaacgc taccagcctc gggctgaacc agtc                              34
```

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 22

```
ggagcccttg ctgctactgt atgct                                       25
```

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 23

```
atcccgggtg gtggtggcgg tgaagttatt ac                               32
```

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 24

```
gcgttaacat gtacaagctg ttggatgcag c                                31
```

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 25

```
acatcgggcc ctcgtgcggc acttc                                       25
```

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 26

```
gcgttaacgc gcggaggaga gcggatcggt tag                              33
```

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 27

```
gcgagctcga gcatgccata tacagtaggt gtg                              33
```

<210> SEQ ID NO 28
<211> LENGTH: 34
<212> TYPE: DNA

```
<213> ORGANISM: Artificial Sequence
<220> FEATURE:
<223> OTHER INFORMATION: Description of Artificial Sequence: Primer

<400> SEQUENCE: 28
gcgatatcga tttgcaaggg cgaagtgcac aaga                              34

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 29
gcgatatcga aggcagaagg caactcccag tt                                32

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 30
cactcccaca ccacacctac caggca                                      26

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 31
gggcttcgtg agccatgaat ccctt                                       25

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 32
atcccgggcg tggaaggaga ggcgaatgtg gagg                              34

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 33
gcgagctcct gtgggtgtct agcttcaggt tc                                32

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 34
gcgctgcaga tttcatttgg agaggacacg                                   30
```

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 35
cgcggccggc ctcagaagaa ctcgtcaaga aggcg                              35

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 36
gctgacacgc caagcctcgc tagtc                                         25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 37
gcagacgtat gggaactagc cacct                                         25

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 38
cgctctacga ttcggtaggt gagagc                                        26

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 39
ctggcgacag aggaggacgc gttgt                                         25

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 40
gcgtaggctc ttctacatct cgcaac                                        26

<210> SEQ ID NO 41
<211> LENGTH: 27
<212> TYPE: DNA
<213> ORGANISM: Artificial Sequence
<220> FEATURE:

```
<223> OTHER INFORMATION: Description of Artificial Sequence: Primer

<400> SEQUENCE: 41
cggacgatct tggtggagga gtggaac                                          27

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 42
gtgtcgagcg atggagacag accac                                            25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 43
cggatggatg agatgatgaa gggag                                            25

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 44
cacgaccacc atggacgaag cctcca                                           26

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 45
ggctgtgctc ggtagattct ctcgca                                           26

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 46
cagcctcttg gttggacaag tgctc                                            25
```